United States Patent
George et al.

(10) Patent No.: US 12,173,266 B1
(45) Date of Patent: Dec. 24, 2024

(54) DEVICES AND METHODS FOR PREPARING IN VITRO MODELS OF NEUROMUSCULAR JUNCTIONS

(71) Applicant: ANANDA DEVICES INC., Laval (CA)

(72) Inventors: Subin Mac George, Orleans (CA); Lindsay Morgan Kuyltjes, Montreal (CA); Margaret Haiganouch Magdesian, Saint-Laurent (CA)

(73) Assignee: ANANDA DEVICES INC., Laval (CA)

( * ) Notice: Subject to any disclaimer, the term of this patent is extended or adjusted under 35 U.S.C. 154(b) by 0 days.

(21) Appl. No.: 18/367,918

(22) Filed: Sep. 13, 2023

Related U.S. Application Data

(63) Continuation of application No. PCT/CA2023/050340, filed on Mar. 16, 2023.

(60) Provisional application No. 63/269,413, filed on Mar. 16, 2022.

(51) Int. Cl.
  *C12M 1/12* (2006.01)
  *C12M 1/42* (2006.01)

(52) U.S. Cl.
  CPC ............ *C12M 25/00* (2013.01); *C12M 35/02* (2013.01)

(58) Field of Classification Search
  CPC ....... C12M 23/16; C12M 25/00; C12M 35/02
  See application file for complete search history.

(56) References Cited

U.S. PATENT DOCUMENTS

| | | | |
|---|---|---|---|
| 2011/0306041 A1* | 12/2011 | Viovy | C12N 5/0619 |
| | | | 435/7.1 |
| 2017/0355945 A1* | 12/2017 | Kamm | C12M 21/08 |
| 2021/0380913 A1 | 12/2021 | Shimizu et al. | |

FOREIGN PATENT DOCUMENTS

EP  3450540 A1  3/2019

OTHER PUBLICATIONS

PCT/CA2023/050340; International Search Report and Written Opinion mailed Jun. 13, 2023.
Osaki et al., "Microphysiological 3D model of amyotrophic lateral sclerosis (ALS) from human iPS-derived muscle cells and optogenetic motor neurons", Science Advances, 4: 1-15 (2018).
Osaki et al., "On-chip 3D neuromuscular model for drug screening and precision medicine in neuromuscular disease", Nature Protocols, 15: 421-449 (2020).

(Continued)

*Primary Examiner* — Jonathan M Hurst

(57) ABSTRACT

There are provided a cell culture device and associated method for preparing an in vitro model of a neuromuscular junction (NMJ). The cell culture device can include a cell culture layer that includes a neuronal cells channel for receiving neuronal cells therein, and a neuromuscular junction chamber in fluid communication with the neuronal cells channel to receive muscle cells therein to enable co-culture of the neuronal cells with the muscle cells and form the NMJ. The neuronal cells channel includes a first portion having a first portion cross-section and a second portion having a second portion cross-section that is smaller than the first portion cross-section and provided downstream of the first portion to retain neuronal cells. The neuromuscular junction chamber can optionally include pillars for culturing muscle cells therebetween. The in vitro model can be used for analysing a biological material from a patient or diagnose a condition, for instance.

26 Claims, 22 Drawing Sheets

(56) References Cited

OTHER PUBLICATIONS

Uzel et al., "Microfluidic device for the formation of optically excitable, three-dimensional, compartmentalized motor units", Science Advances, 2: 1-13 (2016).
Guo et al. "A Human-Based Functional NMJ System for Personalized ALS Modeling and Drug Testing" 2020.
Malik et al. Critical Considerations for the Design of Multi-Organ Microphysiological Systems 2021.
Mills et al. "Neurturin is a PGC-1α1 controlled myokine that promotes motor neuron recruitment and neuromuscular junction formation" 2017.
Santhanam et al. "Stem cell dervised phenotypic human neuromuscular junction model for dose response evaluation of therapeutics" 2018.

\* cited by examiner

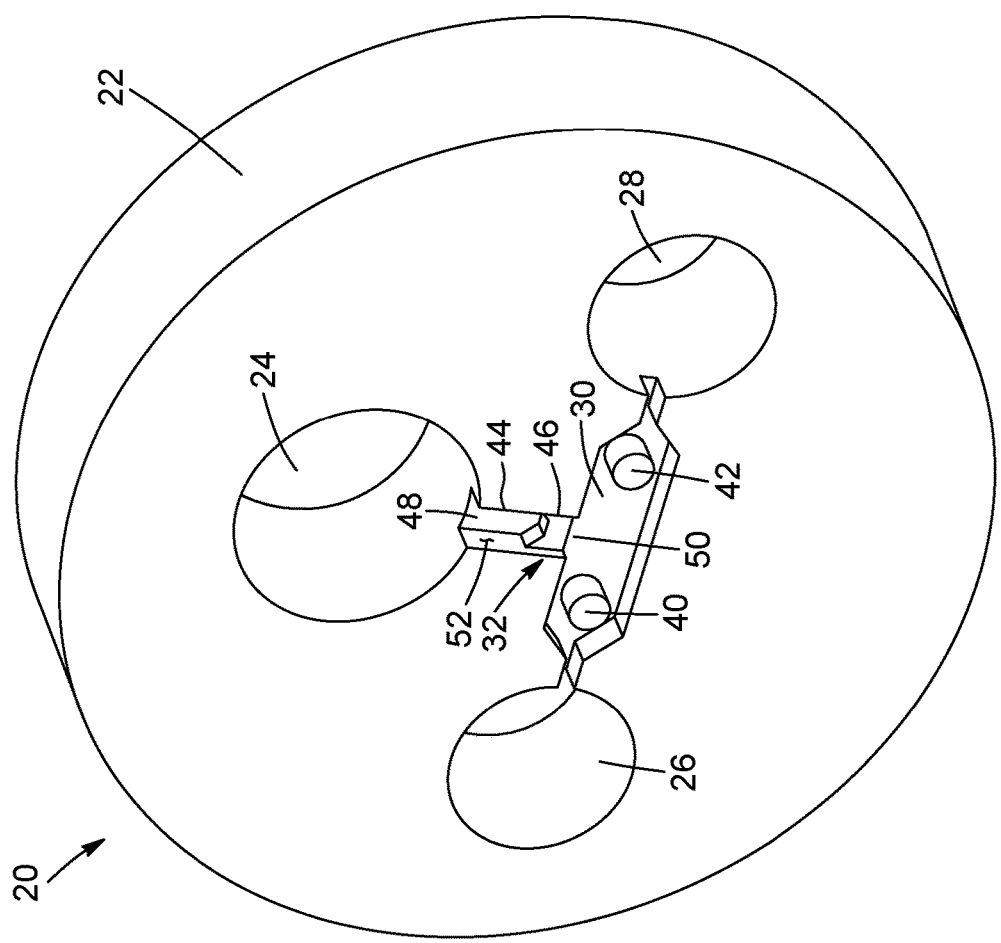
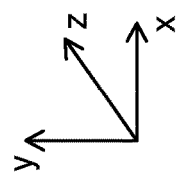
FIG. 3A

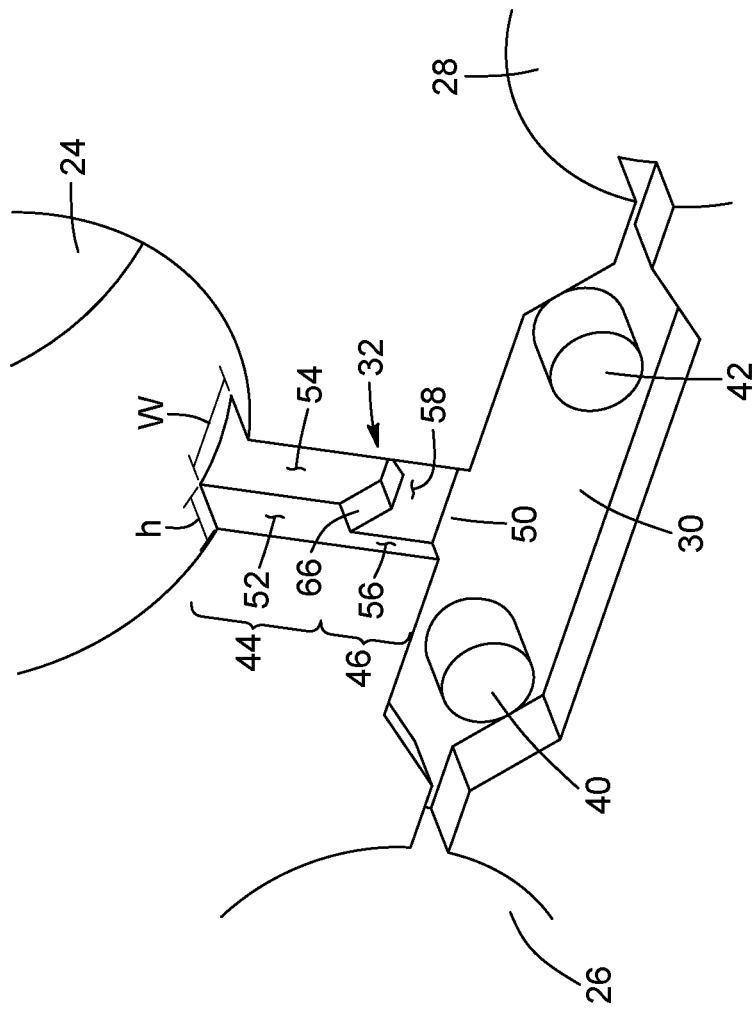
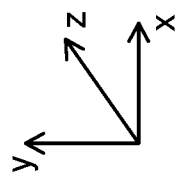
FIG. 3B

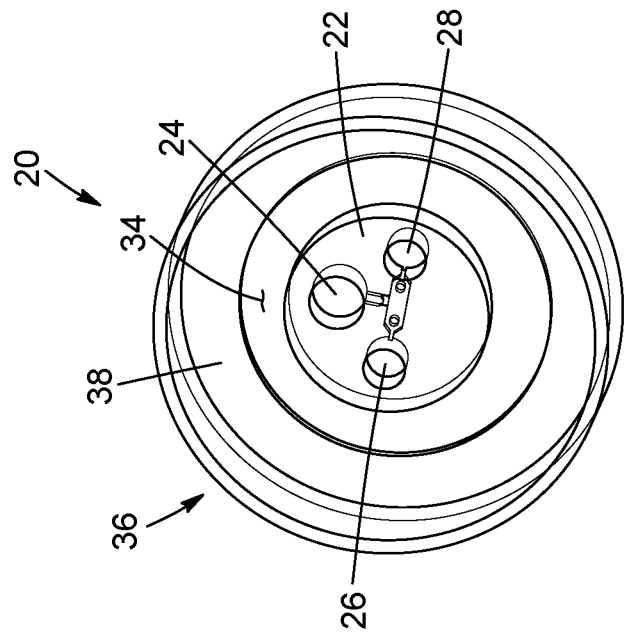
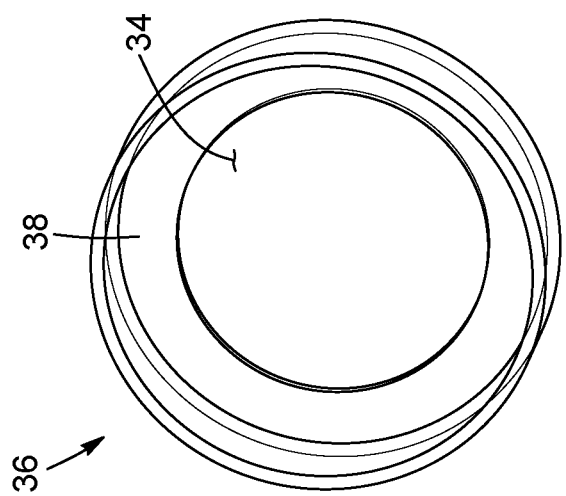
FIG. 6B
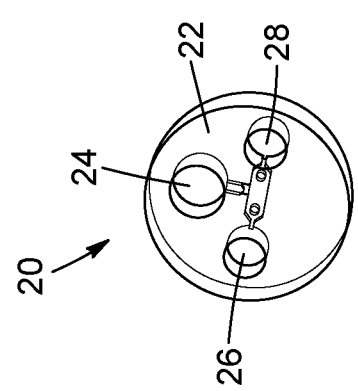
FIG. 6A

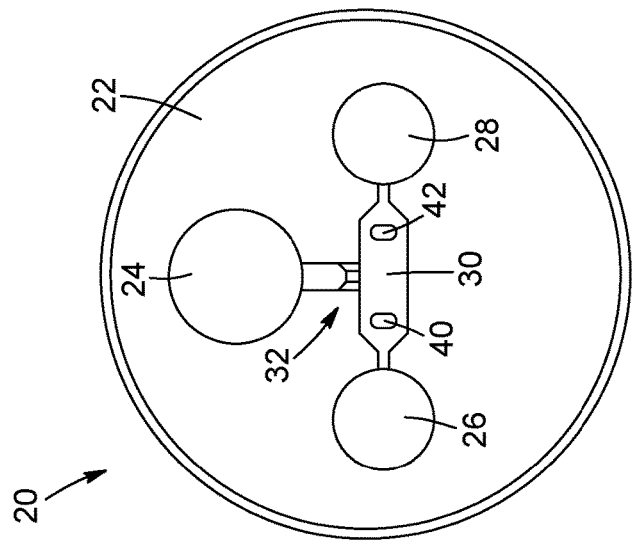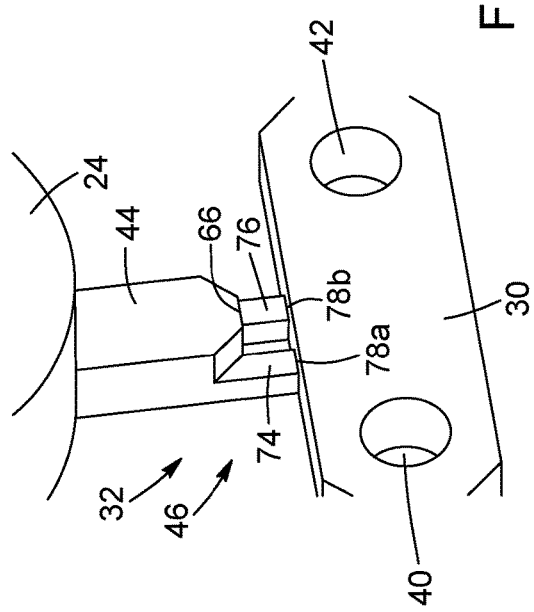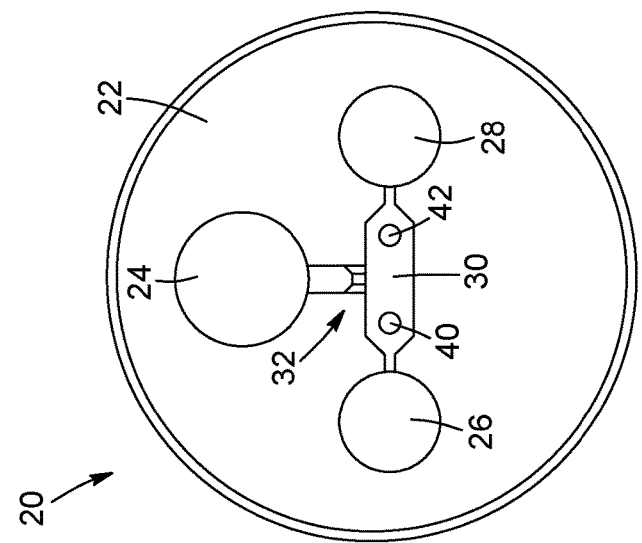

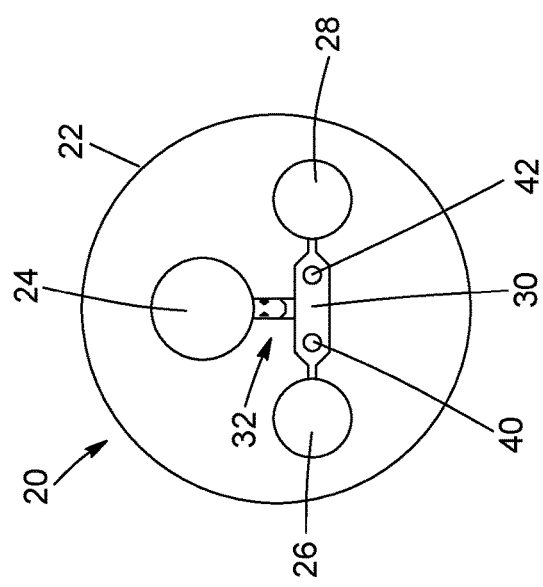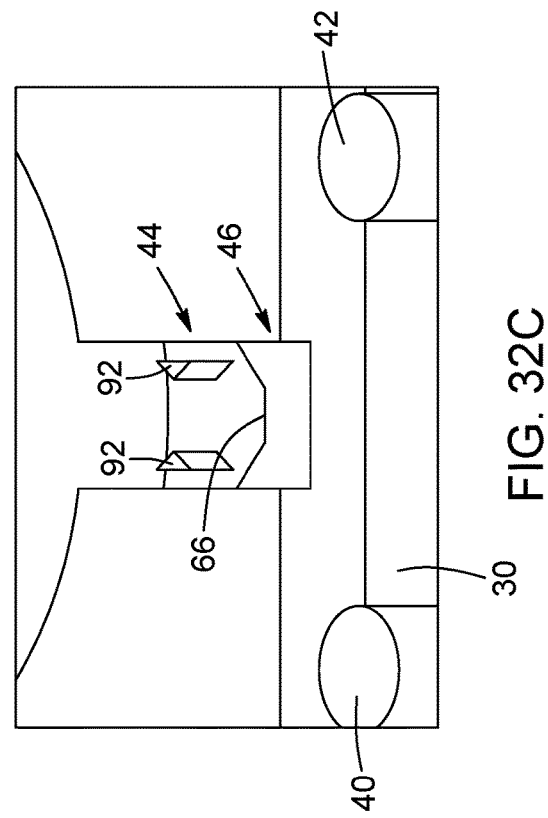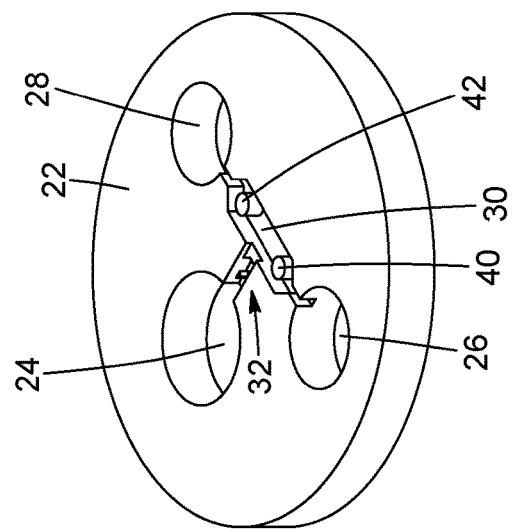

DEVICES AND METHODS FOR PREPARING IN VITRO MODELS OF NEUROMUSCULAR JUNCTIONS

This is a continuation of PCT Application PCT/CA2023/050340 filed on Mar. 16, 2023, which claims Priority to U.S. Application No. 63/269,413 filed on Mar. 16, 2022. The entire contents of these applications are incorporated herein by reference in their entireties.

TECHNICAL FIELD

The technical field generally relates to cell culture techniques. More particularly, the technical field relates to systems, devices and methods for preparing in vitro models of neuromuscular junctions.

BACKGROUND

The neuromuscular junction (NMJ) is a synaptic connection between the terminal end of a motor nerve and a muscle, which can be for instance skeletal muscle, cardiac muscle or smooth muscle. The NMJ is the site for the transmission of action potential from the nerve to the muscle. The NMJ is also a site susceptible to many diseases and a site of action for various pharmacological drugs. NMJs work as an interface to translate an action potential from a presynaptic motor neuron in a contraction of a postsynaptic myofiber to enable muscle contraction, thus governing muscle contraction from the central nervous system to the muscle fibers. More specifically, when an action potential reaches a presynaptic motor neuron and activates voltage-gated calcium channels, calcium flows inward into the neuron and triggers the diffusion of acetylcholine (ACh) across the synaptic cleft to the acetylcholine receptors (AChRs) on the postsynaptic myofiber, resulting in the opening of cation channels and producing depolarization of the myofiber.

NMJs are affected at early stages of numerous neurodegenerative and neuroimmunological diseases. NMJs are also the target of several poisons, toxins and nervous agents. Accordingly, the design of appropriate experimental NMJ models is important to produce efficient and reliable approaches to study NMJ development and function, but also to generate conditions that recapitulate distinct features of diseases.

However, efforts to date have proven difficult to systematically study and manipulate NMJs in live subjects. Although animal models have been used in the past to study NMJs, there are differences between the human synapse compared to other mammalian synapses, which can affect the transferability of results from animal models to humans. Furthermore, in vitro models of NMJs have been developed, both mammalian and non-mammalian, to try to mimic an in vivo environment to culture muscle cells and motor neurons, but these current models also have various limitations.

Thus, there is a need for improved in vitro models of NMJs developed with both healthy and diseased cells, for instance to enable mechanistic and drug development studies.

SUMMARY

In accordance with an aspect, there is provided a cell culture device for preparing an in vitro model of a neuromuscular junction, the cell culture device comprising:

a cell culture layer comprising:
  a neuronal cells inlet configured for receiving neuronal cells therein;
  first and second muscle cells reservoirs, wherein at least one of the first and second muscle cells reservoirs is configured for seeding muscle cells therein;
  a neuromuscular junction chamber extending between the first and second muscle cells reservoirs and in fluid communication therewith to enable co-culture of the neuronal cells with the muscle cells to form the neuromuscular junction; and
  a neuronal cells channel extending between the neuronal cells inlet and the neuromuscular junction chamber and in fluid communication therewith, the neuronal cells channel comprising:
    a first portion having a first portion cross-section sized to retain neural cell bodies of the neuronal cells; and
    a second portion provided downstream of the first portion, the second portion having a second portion cross-section smaller than the first portion cross-section and that is sized to prevent entry of the neural cell bodies therein.

In some implementations, the first portion comprises first portion sidewalls, a first portion front wall and a first portion back wall, and the second portion comprises second portion sidewalls, a second portion front wall and a second portion back wall.

In some implementations, a sidewall transition from the first portion sidewalls to the second portion sidewalls is substantially linear, such that the neuronal cells channel has a channel width that is substantially the same between the first portion and the second portion.

In some implementations, the first portion sidewalls and the second portion sidewalls are provided such that the neuronal cells channel has a channel width that is smaller in the second portion compared to the first portion.

In some implementations, the cell culture device further comprises a cell culture dish, a cell culture plate or a microscope slide having a cell culture layer receiving surface onto which the cell culture layer is deposited.

In some implementations, the first portion back wall is provided by the cell culture layer receiving surface of the cell culture dish, the cell culture plate or the microscope slide.

In some implementations, the first portion back wall and the second portion back wall are provided by the cell culture layer receiving surface of the cell culture dish, the cell culture plate or the microscope slide.

In some implementations, the second front wall is provided inwardly from the first front wall, such that the neuronal cells channel has a channel height that smaller in the second portion compared to the first portion, thereby providing at least in part the smaller second portion cross-section compared to the first portion cross-section.

In some implementations, the second back wall is provided inwardly from the first back wall, such that the neuronal cells channel has a channel height that smaller in the second portion compared to the first portion, thereby providing the smaller second portion cross-section compared to the first portion cross-section.

In some implementations, at least one of the second front wall and the second back wall is provided inwardly from the first front wall and the first back wall respectively, such that the neuronal cells channel has a channel height that smaller in the second portion compared to the first portion, thereby providing the smaller second portion cross-section compared to the first portion cross-section.

In some implementations, the channel height varies from the first portion to the second portion according to a ratio ranging from about 2 to about 12.

In some implementations, the channel height varies from the first portion to the second portion according to a ratio ranging from about 3 to about 9.

In some implementations, the first portion of the neuronal cells channel comprises a frustoconical converging portion converging inwardly.

In some implementations, the first portion of the neuronal cells channel comprises a frustopyramidal converging portion converging inwardly.

In some implementations, a transition from the first portion front wall to the second portion front wall comprises a step change defining an abutting wall extending transversally across at least a portion of the neuronal cells channel.

In some implementations, the abutting wall converges inwardly toward a centerline of the neuronal cells channel.

In some implementations, the abutting wall includes a curvature.

In some implementations, the abutting wall is substantially flat.

In some implementations, the abutting wall comprises a plurality of inwardly converging planes.

In some implementations, the cell culture device further comprises a first pillar provided in the neuromuscular junction chamber in proximity of the first muscle cells reservoir and a second pillar provided in the neuromuscular junction chamber in proximity of the second muscle cells reservoir, the first and second pillars extending upwardly and serving as respective anchoring locations for the muscle cells.

In some implementations, the cell culture device further comprises a gel seeding inlet in fluid communication with the neuromuscular junction chamber and opposed to the neuronal cells inlet, the gel seeding inlet being configured to seed gel in the neuromuscular junction chamber.

In some implementations, the neuronal cells are provided as a cluster of neuronal cell bodies and include axons extending away from the cell bodies, the first portion of the neuronal cells channel being configured to receive the cluster of cell bodies and the second portion of the neuronal cells channel being configured to direct the axons toward the neuromuscular junction chamber.

In some implementations, the second portion of the neuronal cells channel comprises microchannels for directing axonal growth.

In some implementations, the neuronal cells are provided as a neurosphere.

In some implementations, the neuronal cells are provided as a neuro-organoid.

In some implementations, the neuronal cells comprises motor neurons.

In some implementations, at least one of the neuronal cells inlet, the first muscle cells reservoir and the second muscle cells reservoir is configured to receive a test substance therein.

In some implementations, the cell culture device further comprises an electrode provided in proximity of the cell culture layer.

In some implementations, the electrode forms part of an electrode layer.

In some implementations, the electrode layer is located underneath the cell culture layer or superposed to the cell culture layer.

In some implementations, the electrode layer is integrated in the cell culture layer.

In some implementations, the electrode comprises a plurality of electrodes.

In some implementations, the electrode comprises at least one of a metallic electrode, a metal oxide electrode, a carbon electrode, a multi electrode array, and a field effect transistor detector.

In some implementations, the electrode is configured for stimulating the neuronal cells.

In some implementations, the electrode is configured for stimulating the muscle cells.

In some implementations, the electrode is configured to perform at least one of collecting, recording, measuring, and detecting a response of the neuronal cells to stimulation.

In some implementations, the electrode is configured to perform at least one of collecting, recording, measuring, and detecting a response of the muscle cells to stimulation.

In some implementations, the cell culture device further comprises an electronic device in ohmic connection with the electrode.

In some implementations, the cell culture device further comprises a sensor configured for stimulating the neuronal cells, measuring a response from the neuronal cells to stimulation, providing an output or receiving an input.

In some implementations, the cell culture device further comprises a sensor configured for stimulating the muscle cells, measuring a response from the neuronal cells to stimulation, providing an output or receiving an input.

In some implementations, the sensor comprises an optical or an electrical transducer.

In some implementations, the second portion of the neuronal cells channel includes longitudinally extending supports to prevent downstream movement toward the neuromuscular junction chamber.

In some implementations, the first portion of the neuronal cells channel includes an hourglass section to prevent upstream movement toward the neuronal cells inlet.

In some implementations, the first portion of the neuronal cells channel includes posts to prevent upstream movement toward the neuronal cells inlet.

In some implementations, the cell culture device comprises one or more features as defined herein and/or as described and/or illustrated herein.

In accordance with another aspect, there is provided a cell culture device for preparing an in vitro model of a neuromuscular junction, the cell culture device comprising:
  a cell culture layer comprising:
    a neuronal cells channel configured for receiving neuronal cells therein and comprising:
      a first portion having a first portion cross-section; and
      a second portion having a second portion cross-section smaller than the first portion cross-section and provided downstream of the first portion; and
    a neuromuscular junction chamber in fluid communication with the neuronal cells channel and configured to receive muscle cells therein to enable co-culture of the neuronal cells with the muscle cells and form the neuromuscular junction, the neuromuscular junction chamber comprising:
      first and second pillars provided in a spaced-apart relationship on either side of the neuronal cells channel for culturing the muscle cells therebetween.

In some implementations, the first portion comprises first portion sidewalls, a first portion front wall and a first portion back wall, and the second portion comprises second portion sidewalls, a second portion front wall and a second portion back wall.

In some implementations, a sidewall transition from the first portion sidewalls to the second portion sidewalls is substantially linear, such that the neuronal cells channel has a channel width that is substantially the same between the first portion and the second portion.

In some implementations, the first portion sidewalls and the second portion sidewalls are provided such that the neuronal cells channel has a channel width that is smaller in the second portion compared to the first portion.

In some implementations, the cell culture device further comprises a cell culture dish, a cell culture plate or a microscope slide having a cell culture layer receiving surface onto which the cell culture layer is deposited.

In some implementations, the first portion back wall is provided by the cell culture layer receiving surface of the cell culture dish, the cell culture plate or the microscope slide.

In some implementations, the first portion back wall and the second portion back wall are provided by the cell culture layer receiving surface of the cell culture dish, the cell culture plate or the microscope slide.

In some implementations, the second front wall is provided inwardly from the first front wall, such that the neuronal cells channel has a channel height that smaller in the second portion compared to the first portion, thereby providing at least in part the smaller second portion cross-section compared to the first portion cross-section.

In some implementations, the second back wall is provided inwardly from the first back wall, such that the neuronal cells channel has a channel height that smaller in the second portion compared to the first portion, thereby providing the smaller second portion cross-section compared to the first portion cross-section.

In some implementations, at least one of the second front wall and the second back wall is provided inwardly from the first front wall and the first back wall respectively, such that the neuronal cells channel has a channel height that smaller in the second portion compared to the first portion, thereby providing the smaller second portion cross-section compared to the first portion cross-section.

In some implementations, the channel height varies from the first portion to the second portion according to a ratio ranging from about 2 to about 12.

In some implementations, the channel height varies from the first portion to the second portion according to a ratio ranging from about 3 to about 9.

In some implementations, the first portion of the neuronal cells channel comprises a frustoconical converging portion converging inwardly.

In some implementations, the first portion of the neuronal cells channel comprises a frustopyramidal converging portion converging inwardly.

In some implementations, a transition from the first portion front wall to the second portion front wall comprises a step change defining an abutting wall extending transversally across a portion of the neuronal cells channel.

In some implementations, the abutting wall converges inwardly toward a centerline of the neuronal cells channel.

In some implementations, the abutting wall includes a curvature.

In some implementations, the abutting wall is substantially flat.

In some implementations, the abutting wall comprises a plurality of inwardly converging planes.

In some implementations, the cell culture layer further comprises a gel seeding inlet in fluid communication with the neuromuscular junction chamber and opposed to the neuronal cells inlet to seed gel in the neuromuscular junction chamber.

In some implementations, the neuronal cells are provided as a cluster of neuronal cell bodies and axons extending away from the cell bodies, the first portion of the neuronal cells channel being configured to receive the cluster of cell bodies and the second portion of the neuronal cells channel being configured to direct the axons toward the neuromuscular junction chamber.

In some implementations, the second portion of the neuronal cells channel comprises microchannels for directing axonal growth.

In some implementations, the neuronal cells are provided as a neurosphere.

In some implementations, the neuronal cells are provided as a neuro-organoid.

In some implementations, the neuronal cells comprise motor neurons.

In some implementations, the neuronal cells inlet is configured to receive a test substance therein such that the test substance reaches the neuromuscular junction chamber.

In some implementations, the second portion of the neuronal cells channel includes longitudinally extending supports to prevent downstream movement toward the neuromuscular junction chamber.

In some implementations, the first portion of the neuronal cells channel includes an hourglass section to prevent upstream movement toward the neuronal cells inlet.

In some implementations, the first portion of the neuronal cells channel includes posts to prevent upstream movement toward the neuronal cells inlet.

In some implementations, the cell culture device comprises one or more features as defined herein and/or as described and/or illustrated herein.

In accordance with another aspect, there is provided a method for preparing an in vitro model of a neuromuscular junction, the method comprising:
  supplying neuronal cells to a neuronal cells channel provided in a cell culture layer, the neuronal cells channel comprising:
    a first portion having a first portion cross-section; and
    a second portion having a second portion cross-section smaller than the first portion cross-section and provided downstream of the first portion;
  supplying muscle cells to a neuromuscular junction chamber provided in the cell culture layer and in fluid communication with the neuronal cells channel to enable co-culture of the neuronal cells with the muscle cells and form the neuromuscular junction.

In some implementations, supplying the muscle cells to the neuromuscular junction chamber comprises supplying the muscle cells suspended in a gel solution.

In some implementations, the gel solution comprises an extracellular membrane matrix (ECM) material.

In some implementations, the gel solution comprises one or more of Matrigel® Geltrex®, fibrin or collagen.

In some implementations, the neuronal cells are provided as a three-dimensional neuronal assembly of the neuronal cells.

In some implementations, the three-dimensional neuronal assembly comprises at least one of a neurosphere, a spheroid, a neural aggregate, or a neuro-organoid.

In accordance with another aspect, there is provided a method for analysing a biological material from a patient using an in vitro model of a neuromuscular junction, the method comprising:
  supplying neuronal cells to a neuronal cells channel provided in a cell culture layer, the neuronal cells channel comprising:
    a first portion having a first portion cross-section; and
    a second portion having a second portion cross-section smaller than the first portion cross-section and provided downstream of the first portion;
  supplying muscle cells to a neuromuscular junction chamber provided in the cell culture layer and in fluid communication with the neuronal cells channel to enable co-culture of the neuronal cells with the muscle cells and form the neuromuscular junction;
  contacting at least one of the neuronal cells and the muscular cells with the biological material from the patient; and
  measuring a functionality parameter related to the neuromuscular junction.

In some implementations, the functionality parameter comprises at least one of a contraction force from the muscle cells, a contraction duration of the muscle cells, a neuronal cells viability, a muscle cells viability, a neuronal cells survival rate, a muscle cells survival rate, and an electrical signal from the neuronal cells or from the muscle cells.

In some implementations, the method further comprises adding a test substance to at least one of the neuronal cells channel and the neuromuscular junction chamber, and wherein the determining the functionality parameter related to the neuromuscular junction is performed subsequently to the addition of the test substance.

In some implementations, the test substance comprises at least one of a biological material and a chemical material.

In some implementations, the biological material comprises at least one of an antibody, an antibody fragment, an antigen, an antigen fragment, a toxin, an enzyme, a DNA fragment, an RNA fragment, a virus, and a bacteria.

In some implementations, the chemical material comprises at least one of drug and a chemical compound.

In accordance with another aspect, there is provided a method for analysing a neuromuscular junction, the method comprising:
  supplying neuronal cells to a neuronal cells channel provided in a cell culture layer, the neuronal cells channel comprising:
    a first portion having a first portion cross-section; and
    a second portion having a second portion cross-section smaller than the first portion cross-section and provided downstream of the first portion;
  supplying muscle cells to a neuromuscular junction chamber provided in the cell culture layer and in fluid communication with the neuronal cells channel to enable co-culture of the neuronal cells with the muscle cells and form the neuromuscular junction;
  contacting at least one of the neuronal cells and the muscular cells with a test substance; and
  measuring a functionality parameter related to the neuromuscular junction.

In some implementations, the functionality parameter comprises at least one of a contraction force from the muscle cells, a contraction duration of the muscle cells, a neuronal cells viability, a muscle cells viability, a neuronal cells survival rate, a muscle cells survival rate, and an electrical signal from the neuronal cells or from the muscle cells.

In some implementations, the test substance comprises at least one of a biological material and a chemical material.

In some implementations, the biological material comprises at least one of a biological fluid or a biological tissue from a patient, an antibody, an antibody fragment, an antigen, an antigen fragment, a toxin, an enzyme, a DNA fragment, an RNA fragment, a virus, and a bacteria.

In some implementations, the chemical material comprises at least one of drug and a chemical compound.

In accordance with another aspect, there is provided a method for diagnosing a condition of a patient using an in vitro model of a neuromuscular junction, the method comprising:
  supplying a biological material from the patient to a cell culture device comprising:
    a cell culture layer comprising:
      a neuronal cells channel configured for receiving neuronal cells therein and comprising:
        a first portion having a first portion cross-section; and
        a second portion having a second portion cross-section smaller than the first portion cross-section and provided downstream of the first portion; and
      a neuromuscular junction chamber in fluid communication with the neuronal cells channel and configured to receive muscle cells therein to enable co-culture of the neuronal cells with the muscle cells and form the neuromuscular junction; and
  determining a functionality parameter related to the neuromuscular junction, wherein the functionally parameter provides information related to the condition of the patient.

In some implementations, the functionality parameter comprises at least one of a contraction force from the muscle cells, a contraction duration of the muscle cells, a neuronal cells viability, a muscle cells viability, a neuronal cells survival rate, a muscle cells survival rate, and an electrical signal from the neuronal cells or from the muscle cells.

In some implementations, the method further comprises adding a test substance to at least one of the neuronal cells channel and the neuromuscular junction chamber.

In some implementations, determining the functionality parameter related to the neuromuscular junction is performed subsequently to the addition of the test substance.

In some implementations, determining the functionality parameter related to the neuromuscular junction is performed prior to and subsequent to the addition of the test substance.

In some implementations, the method comprises one or more features as defined herein and/or as described and/or illustrated herein.

BRIEF DESCRIPTION OF THE DRAWINGS

The attached figures illustrate various features, aspects and implementations of the technology described herein.

FIG. 3A is a bottom perspective view of the cell culture device of FIG. 1.

FIG. 3B is an enlarged view of a portion of the cell culture device of FIG. 3B, showing a portion of the neuronal cells inlet, a portion of the first muscle cells reservoir and a portion of the second muscle cells reservoir, the neuromuscular junction chamber, the neuronal cells channel and the two pillars.

FIG. 6A is a front perspective view of the cell culture device of FIG. 1 and of a cell culture dish.

FIG. 6B is a front perspective view of the cell culture device and the cell culture dish shown in FIG. 6A, with the cell culture device being shown deposited onto a cell culture layer receiving surface of the cell culture dish.

FIG. 19 is a bottom view of a cell culture device that includes a cell culture layer having a neuronal cells inlet, a first muscle cells reservoir, a second muscle cells reservoir, a neuronal cells channel that includes first and second channels, and a neuromuscular junction chamber that includes two cylindrical pillars.

FIG. 20 is a bottom view of a cell culture device that includes a cell culture layer having a neuronal cells inlet, a first muscle cells reservoir, a second muscle cells reservoir, a neuronal cells channel that includes first and second channels, and a neuromuscular junction chamber that includes two elliptical pillars.

FIG. 21 is an enlarged front perspective view of a mold for producing the cell culture device shown in FIG. 19.

FIG. 32A is a bottom view of a cell culture device that includes a cell culture layer having a neuronal cells inlet, a first muscle cells reservoir, a second muscle cells reservoir, a neuronal cells channel having an abutment wall, a neuromuscular junction chamber that includes two pillars and posts provided in a first portion of the neuronal cells channel.

FIG. 32B is a bottom perspective view of the cell culture device of FIG. 32A.

FIG. 32C is an enlarged view of the neuronal cells channel of the cell culture layer of FIG. 32A.

DETAILED DESCRIPTION

Figure 1:
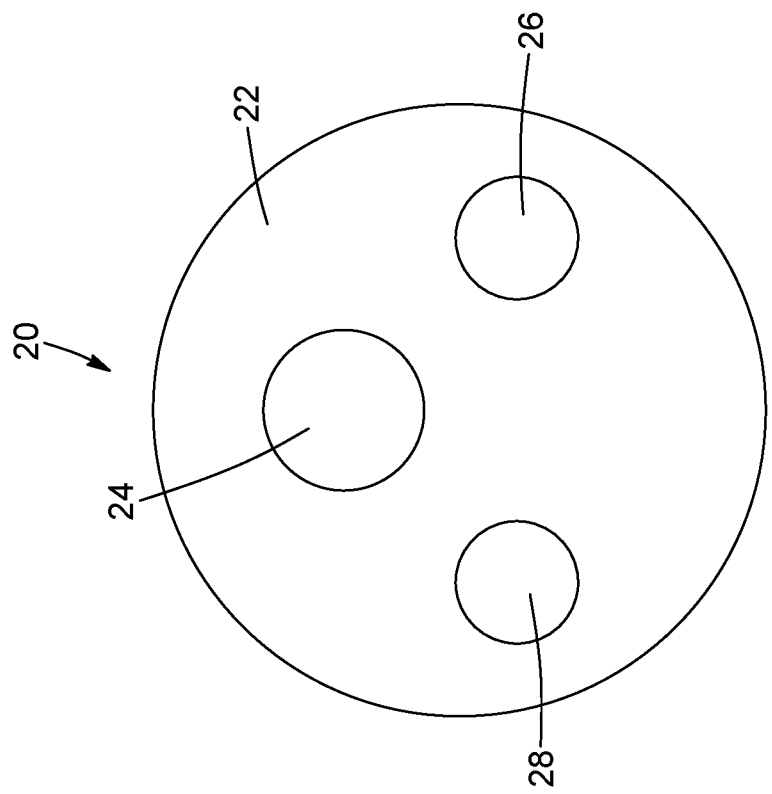
FIG. 1 is a bottom view of a cell culture device that includes a cell culture layer having a neuronal cells inlet, a first muscle cells reservoir, a second muscle cells reservoir, a neuronal cells channel having an abutment wall, and a neuromuscular junction chamber that includes two pillars.

Techniques described herein relate to systems, devices and methods for preparing an in vitro model of a neuromuscular junction (NMJ). The in vitro models as described herein can be used for a wide range of cellular assays including compound screening, compound discovery, screening of a patient's derived samples, safety, and efficacy testing, etc. The in vitro models as described herein can also be used to perform mechanistic studies related to the development and maturation of NMJs and mechanisms involved in the regulation and function of NMJs, and to model neurological diseases and disorders, immunological diseases and neuroimmunological diseases, among others.

The in vitro models of NMJ described herein can be obtained as the result of a given configuration and interaction of various reservoirs, or chambers, provided in a cell culture layer that can optionally be used in collaboration with a cell culture plate, a cell culture dish, a microscope slide, or any other surface, such as a surface that includes sensors. Furthermore, as the neuronal cells used for the preparation of the in vitro model of NMJ are typically provided as a three-dimensional neuronal assembly according to various organizations, such as neurospheres, neurospheroids, neural aggregates, neuro-organoids or clusters containing only neuronal cells or in combination with one or more cell types, for instance, neurons and astrocytes, neurons and glia, etc., the size and configuration of certain features of the culture cell layer can be determined at least in part in accordance with the characteristics of the neuronal assembly, and notably its size.

For instance, in some implementations, a cell culture device for preparing an in vitro model of a NMJ can include a cell culture layer comprising a neuronal cells inlet configured for receiving neuronal cells therein, and first and second muscle cells reservoirs. At least one of the first and second muscle cells reservoirs is configured for seeding muscle cells therein. The cell culture layer further includes a neuromuscular junction chamber extending between the first and second muscle cells reservoirs and in fluid communication therewith to enable co-culture of the neuronal cells with the muscle cells and subsequently form the neuromuscular junction. In some implementations, pillars can be provided in the neuromuscular junction chamber to facilitate growth of a bundle of muscle cells therebetween.

In order to provide fluid communication between the neuronal cells inlet and the neuromuscular junction chamber, the cell culture layer includes a neuronal cells channel extending between the neuronal cells inlet and the neuromuscular junction chamber. The neuronal cells channel includes a first portion and a second portion, the first portion being provided in closer proximity to the neuronal cells inlet while the second portion is provided in closer proximity to the neuromuscular junction chamber. In other words, the second portion is provided downstream of the first portion. The first portion has a first portion cross-section and the second portion has a second portion cross-section, the second portion cross-section being smaller than the first portion cross-section. More particularly, the first portion can have a first portion cross-section that is sized to retain neural cell bodies therein, while the second portion can have a second portion cross-section that is sized to prevent entry of the neural cell bodies therein, i.e., to prevent the cell bodies from traveling downstream of the first portion.

As mentioned above, the neuronal cells can be assembled so as to form a neuronal assembly, such as a neurosphere, a neurospheroid, a neuro-organoid or a cluster containing only neuronal cells or in combination with one or more cell types, for instance, neurons and astrocytes, neurons and glia, etc. In such scenarios, the neuronal cells with or without additional cells can be introduced in the cell culture layer via the neuronal cells inlet and migrate toward the first portion of the neuronal cell channel. As mentioned above, the first portion of the neuronal cells channel can be sized to retain the cell bodies of the neuronal cells at a given position within the neuronal cell channel without reaching the neuromuscular junction chamber, while axons can extend away therefrom, i.e., away from the first portion and into the second portion, to reach the neuromuscular junction chamber and interact with the muscle cells to form the NMJ.

It will be appreciated that in the context of the present description, positional terms such as "above", "below", "left", "right", "inwardly", "outwardly", "vertical" and the like should, unless otherwise indicated, be taken in the context of the figures, and should not be considered limiting. When referring to a length, for instance in the context of a length of an axon, it is to be understood that it refers to a measure along a horizontal axis. When referring to a height, for instance in the context of a height of a neuronal cells channel of a cell culture layer as described herein, it is to be understood that it refers to a measure along a vertical axis, once the cell culture layer is placed substantially horizontally on a cell culture plate, a cell culture dish or a microscope slide, for instance. The term "front" is intended to refer to the orientation of the cell culture device once deposited onto a substantially horizontal surface that faces a user, whereas the term "bottom" is intended to refer to the opposite orientation, when a user observes the cell culture device from underneath. The term "outwardly" is intended to refer to a feature that extends towards an exterior side of a reference axis. The term "inwardly" is intended to refer to a feature that extends towards an interior side of a reference axis.

To provide a more concise description, some of the quantitative expressions given herein may be qualified with the term "about". It is understood that whether the term "about" is used explicitly or not, every quantity given herein is meant to refer to an actual given value, and it is also meant to refer to the approximation to such given value that would reasonably be inferred based on the ordinary skill in the art, including approximations due to the experimental and/or measurement conditions for such given value.

Various implementations of the cell culture device will now be described in greater detail.

Cell Culture Device

With reference to FIGS. 1-23, various implementations of a cell culture device 20 are shown. In each of the implementations shown, the cell culture device 20 includes a cell culture layer 22. The cell culture layer 22 can take various forms, and generally includes designated compartments that can be configured for receiving a given type of cells. FIGS. 1-7 illustrate various views of an example implementation of a cell culture layer 22, while FIGS. 8-23 illustrate alternative implementations of a cell culture layer 22. It is to be noted that throughout the figures, the same numerical references refer to similar elements. Furthermore, for the sake of simplicity and clarity, namely so as to not unduly burden the figures with several references numbers, not all figures contain references to all the components and features, and references to some components and features may be found in only one figure, and components and features of the present disclosure which are illustrated in other figures can be easily inferred therefrom. The illustrated implementations, geometrical configurations, materials mentioned and/ or dimensions shown in the figures are optional and are given for exemplification purposes only.

Still referring to FIGS. 1-23, in the implementations shown, each cell culture layer 22 includes a neuronal cells inlet 24, a first muscle cells reservoir 26, and a second muscle cells reservoir 28. The first muscle cells reservoir 26 is longitudinally spaced-apart from the second muscle cell reservoir 28, i.e., spaced-apart along the x-axis of the cell culture layer 22. The neuronal cells inlet 24 is provided offset from the first and second muscle cells reservoirs 26, 28, i.e., between the first and second muscle cells reservoirs 26, 28 and spaced-apart therefrom along the y-axis, the combination of the neuronal cells inlet 24 and the first and second muscle cells reservoirs 26, 28 thus forming a triangular shape.

The cell culture layer 22 further includes a neuromuscular junction chamber 30 extending between the first and second muscle cells reservoirs 26, 28, and a neuronal cells channel 32 extending between the neuronal cells inlet 24 and the neuromuscular junction chamber 30. The neuromuscular junction chamber 30 is configured to be in fluid communication with the first and second muscle cells reservoirs 26, 28, and with the neuronal cells inlet 24 via the neuronal cells channel 32. In the implementations shown, the neuronal cells channel 32 extends substantially perpendicularly relative to the neuromuscular junction chamber 30. In other implementations, the neuronal cells channel 32 can extends at an angle other than 90° relative to the neuromuscular junction chamber 30, i.e., with the neuronal cells inlet 24 being provided closer to the first muscle cells reservoir 26 compared to the second muscle cells reservoir 28, or with the neuronal cells inlet 24 being provided closer to the second muscle cells reservoir 28 compared to the first muscle cells reservoir 26. Thus, it is to be understood that the location of the neuronal cells inlet 24 in the cell culture layer 22 relative to the first and second muscle cells reservoirs 26, 28 can vary from the implementations shown in FIGS. 1-23.

The cell culture layer 22 can be made of any suitable polymeric material into which it is possible to carve, stamp or mold the neuronal cells inlet 24, the first muscle cells reservoir 26, the second muscle cells reservoir 28, the neuromuscular junction chamber 30 and the neuronal cells channel 32. Examples of materials that can be suitable to produce the cell culture layer 22 can include, but are not limited to, polystyrene (PS), cyclo-olefin-copolymer (COC), cycloolefin polymer (COP), polymethyl methacrylate (PMMA), polycarbonate (PC), polyethylene (PE), polyethylene terephthalate (PET), polyamide (Nylon®), polypropylene (PP), polyether ether ketone (PEEK), Teflon®, polydimethylsiloxane (PDMS), and/or thermoplastic elastomer (TPE), as well as synthetic and biological materials such hydrogels, gelatin, collagen, chitosan, etc. In some implementations, the cell culture layer 22 can be made of a polymeric material that is transparent to light in order to facilitate optical analysis and visualization of the neuronal cells in the neuronal cells channel 32 and the muscle cells and the axons in the neuromuscular junction chamber 30.

The cell culture layer 22 can be inserted into a receptacle of a cell culture dish or cell culture plate, onto a microscope slide, or into a well of a multi-well cell culture plate, such as those that are widely available on the market. In other words, the cell culture layer 22 can be configured to be placed onto a cell culture layer receiving surface of a cell culture dish, of a well of a cell culture plate or a microscopic slide, or any other type of receptacle that can be suitable for receiving the cell culture layer 22.

Figure 24:
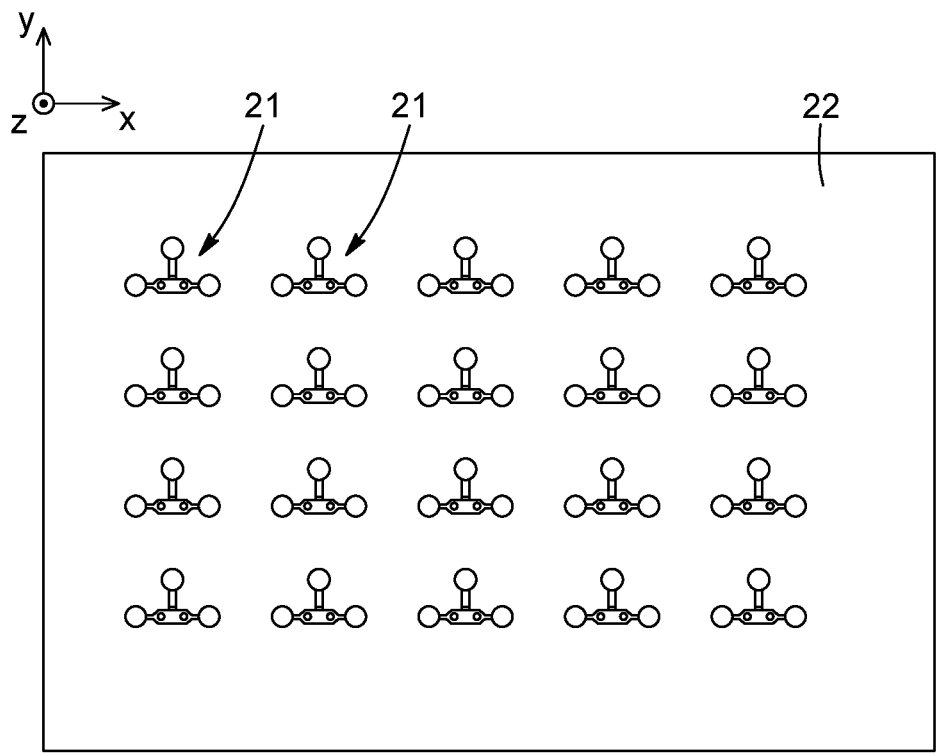
FIG. 24 is a top view of a cell culture layer that includes 20 NMJ preparation units.
Figure 25:
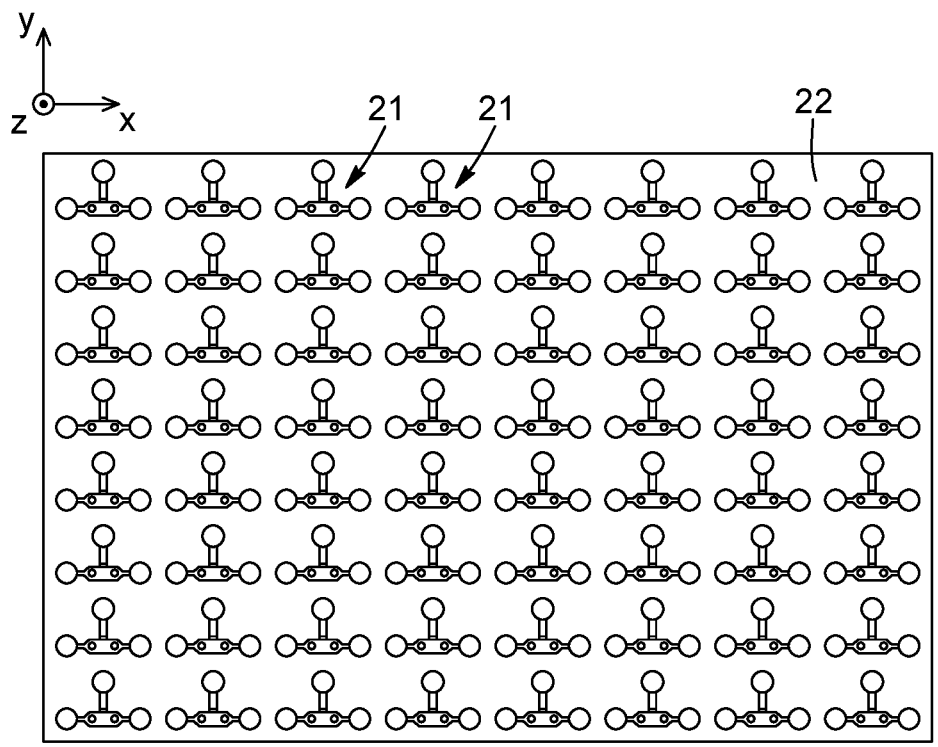
FIG. 25 is a top view of a cell culture layer that includes 64 NMJ preparation units.
Figure 26:
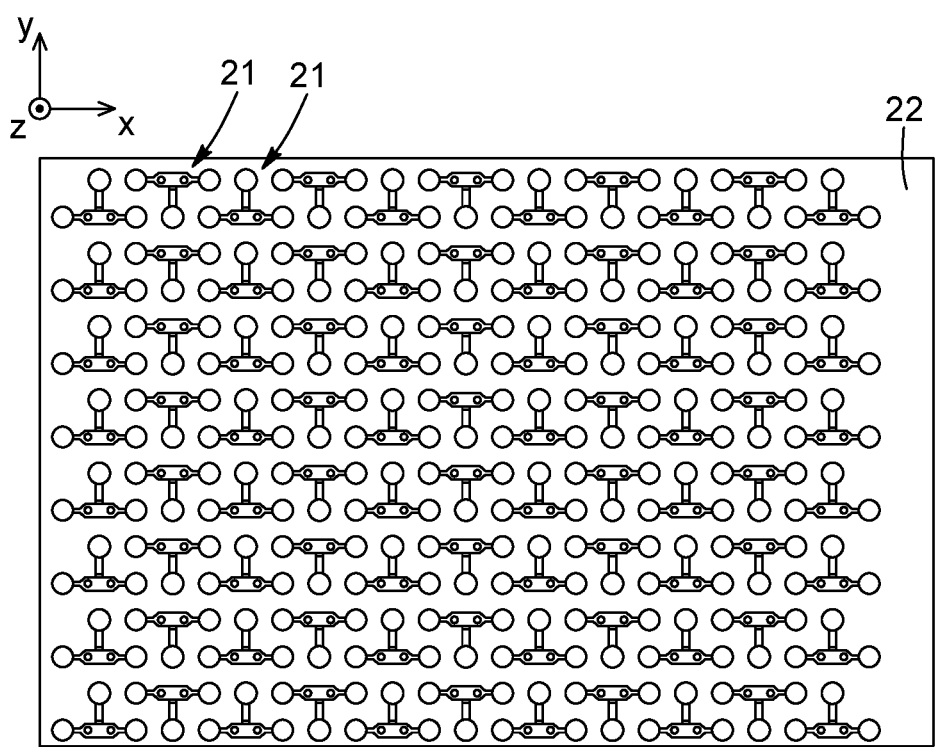
FIG. 26 is a top view of a cell culture layer that includes 88 NMJ preparation units.
Figure 27:
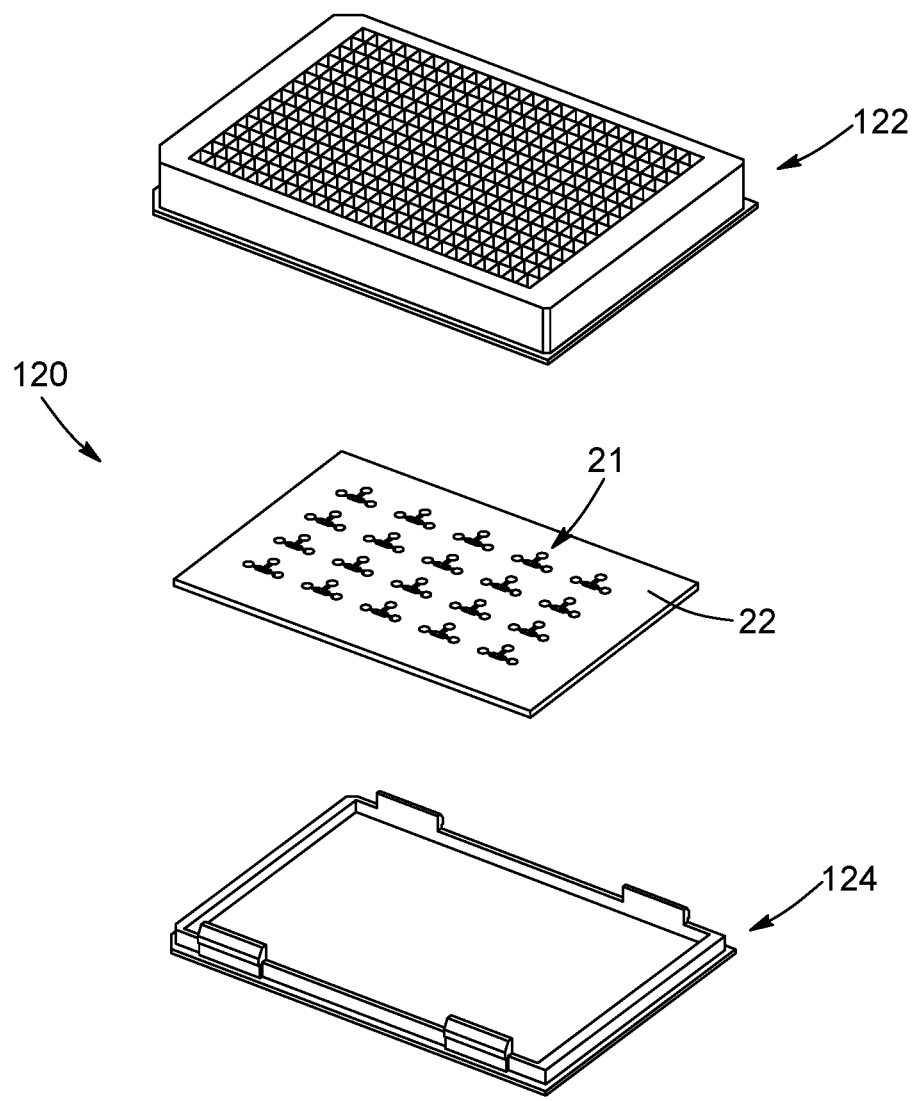
FIG. 27 is an exploded perspective view of a cell culture layer in combination with a cell culture plate that includes a multi-grid layer and a base layer.

The cell culture layer 22 shown in FIGS. 1-23 includes what can be referred to as a single NMJ preparation unit, the NMJ preparation unit including the neuronal cells inlet 24, the first and second muscle cells reservoirs 26, 28, the neuromuscular junction chamber 30 and the neuronal cells channel 32. In alternative implementations, the cell culture layer 22 can include a plurality of NMJ preparation units. The plurality of NMJ preparation units can be provided for instance on a rectangular cell culture layer that can be inserted onto a cell culture layer receiving surface of a cell culture plate. In some implementations, the cell culture plate can be a cell culture plate that complies with American National Standards Institute of the Society for Laboratory Automation and Screening (ANSI/SLAS) microplate standards. The cell culture plate can also be used in cooperation with a multi-well grid layer that is placeable over the cell culture layer and that has a number of wells that corresponds to the number of the NMJ preparation units of the cell culture layer. The multi-well grid layer can also be one that complies with ANSI/SLAS microplate standards. Depending on the needs of a user, the multi-well grid layer may comprise any number of wells, for instance 6, 12, 24, 48, 96, 384, or 1536 wells. FIGS. 24-26 illustrate examples of a cell culture layer 22 that includes 20 NMJ preparation units 21, 64 NMJ preparation units 21 and 88 NMJ preparation units 21, respectively. In the implementation shown in FIG. 26, the NMJ preparation units 21 are provided in an alternate fashion along the x-axis, with a first one of the NMJ preparation units 21, in the upper left hand-side corner, being provided in an upward configuration and a second one of the NMJ preparation units 21, longitudinally adjacent to the first one of the NMJ preparation units 21 along the x-axis, being provided in a downward configuration ("head-to-toe" configuration). In some implementations, this alternance of the upward and downward configurations of the NMJ preparation units 21 can enable providing a higher overall number of NMJ preparation units 21 within a cell culture layer having a given surface area. FIG. 27 illustrates an exploded view of an example of a combination of a cell culture layer 22 and a cell culture plate 120, the cell culture plate 120 comprising a multi-well grid layer 122 and a base layer 124.

In the implementation shown in FIG. 6B, the cell culture layer 22 is shown as being bonded onto a cell culture layer receiving surface 34 of a bottom wall 38 of the cell culture dish 36 shown in FIG. 6A. In some implementations and as exemplified in FIG. 6A, the cell culture dish 36 can have a central cut-out for receiving a glass bottom acting as the bottom wall 38, and the cell culture layer 22 can be bonded to the glass bottom. When the cell culture layer 22 is used with a cell culture plate comprising a plurality of wells, the cell culture layer 22 can be inserted into a corresponding well of the cell culture plate, onto a cell culture layer receiving surface thereof.

The cell culture layer 22 can be reversibly or irreversibly attached to the cell culture layer receiving surface using any suitable method or technique, including but not limited to, compression, surface adhesion, ultrasonic welding, thermocompression bonding, plasma bonding, solvent-assisted bonding, laser-assisted bonding or adhesive bonding using glue or double adhesive tape.

Alternatively, in some implementations, the cell culture layer 22 can be fabricated integral with the bottom wall 38 of the cell culture dish or of the cell culture plate. When the cell culture layer 22 forms an integral part of the cell culture dish or cell culture plate, the resulting device can be manufactured as a single unit. Examples of materials that can be suitable to fabricate the cell culture layer 22 integral with the bottom wall of the cell culture plate can include, but are not limited to, polystyrene (PS), cyclo-olefin-copolymer (COC), cycloolefin polymer (COP), polymethyl methacrylate (PMMA), polycarbonate (PC), polyethylene (PE), polyethylene terephthalate (PET), polyamide (Nylon®), polypropylene or polyether ether ketone (PEEK), Teflon®, polydimethylsiloxane (PDMS), and/or thermoplastic elastomer (TPE), as well as synthetic and biological materials such hydrogels, gelatin, collagen, chitosan, etc.

In the implementations illustrated in FIGS. 1-23, the cell culture layer 22 is configured to extend substantially horizontally once placed in the cell culture dish, the cell culture plate or the microscope slide. Although referring to the cell culture layer 22 as extending substantially horizontally, it is to be understood that the cell culture layer 22 can be provided at a slight angle relative to the cell culture layer receiving surface of the cell culture dish, cell culture plate or microscopic slide onto which it is deposited. In some implementations, providing the cell culture layer 22 at a slight angle relative to the cell culture layer receiving surface of the cell culture dish, cell culture plate or microscopic slide onto which it is deposited can enable selected fluids and/or cells present in given one of the compartments to migrate in a preferential direction.

The cell culture layer 22 can have various sizes and configurations. The size and configuration of the cell culture layer 22 can be adapted to the size and configuration of the receptacle of the cell culture dish or the well of the cell culture plate into which the cell culture layer 22 is intended to be inserted. For instance, for implementations where the cell culture layer 22 is intended to be inserted into a cell culture dish, the size of the cell culture layer 22 can be determined to fit within the receptacle formed by the cell culture dish, as shown in FIGS. 6A-6B. When the cell culture layer 22 is intended for insertion into a well of a multi-well cell culture plate, the size of the cell culture layer 22 can be adapted, e.g., reduced, so that the cell culture layer 22 can fit within a corresponding well of the multi-well cell culture plate.

The neuronal cells inlet 24 is configured to receive an inlet fluid and neuronal cells therein. Examples of types of neuronal cells that can be used for the preparation of the in vitro model of NMJ can include mammalian neurons, such as rodent embryonic neurons, and neurons derived from induced pluripotent stem cells, such as human induced pluripotent stem cells. The option of growing different types of neuronal cells when preparing the in vitro model of NMJ can increase the versatility of the resulting model, which in turn can offer a wider range of opportunities for the various needs of the industry. Using human-derived cells can also be beneficial to provide reproducible and accurate results that can facilitate the translation of the drugs or compounds testing to human studies. In some implementations, diseased neuronal cells from a patient can be used to mimic a given pathological condition, and/or to assess the effect of a given drug for that specific patient. For instance, in some implementations, neuronal cells from a patient suffering from a neuropathy such as amyotropic lateral sclerosis (ALS) and/or a myopathy such as Duchene muscular dystrophy, or an autoimmune disease neuromuscular disease such as myasthenia gravis, or any other neural, muscular or neurodegenerative disease or disorder, can be harvested and cultured to form one or more neurospheres that can subsequently be introduced into the neuronal cells inlet 24 of the cell culture layer 22 as described herein. It is to be understood that any type of neuronal cells, whether healthy or diseased, that can be cultured to form an assembly, such as a neurosphere, is within the scope of the present description.

The inlet fluid can be a cell culture medium that enables survival and/or proliferation of the neuronal cells. In some implementations, the neuronal cells inlet 24 is further configured to receive a test substance therein, such that the neuronal cells present in the neuronal cells inlet 24 and/or in the neuronal cells channel 32 can be exposed to such test substance. As used herein, a test substance can be any type of substance that is desired to be tested to evaluate a response of the NMJ to that test substance, and can include for instance patient-derived fluids (e.g., plasma, serum, blood, urine, etc.) or cells. The test substance can take many forms, and can be for instance a liquid, a suspension, etc.

Either one of the first and second muscle cells reservoirs 26, 28, or both, can be configured to receive a muscle cells reservoir fluid and muscle cells. The muscle cells can be for instance muscle cells dissociated from organs constituting the muscular system, such as from the heart (cardiac cells), limb or body wall muscles (skeletal muscle cells), and visceral muscle (smooth muscle cells), and/or cells that have been differentiated from pluripotent cells, such as muscle cells derived from embryonic stem cells or induced pluripotent stem cells. As described above with respect to the types of neuronal cells that can be used, diseased muscle cells from a patient can also be used to mimic a given pathological condition, and/or to assess the effect of a given drug for that specific patient. For instance, in some implementations, muscle cells from a patient suffering from a neuropathy such as amyotropic lateral sclerosis (ALS) and/or a myopathy such as Duchene muscular dystrophy, or any other neural, muscular or neurodegenerative disease or disorder, can be used. It is to be understood that any type of muscle cells, whether healthy or diseased, is within the scope of the present description.

The muscle cells reservoir fluid can be the same as the inlet fluid or can be different from the inlet fluid. The muscle cells reservoir fluid can be a cell culture medium that enables survival and/or proliferation of the muscle cells received in the first and second muscle cells reservoirs 26, 28 and in the neuromuscular junction chamber 30 of the cell culture layer 22.

In some implementations, the muscle cells reservoir fluid can be a gel solution, such as a gel solution comprising Matrigel®, Geltrex®, fibrin, collagen, or other types of basement membrane matrix or extracellular membrane matrix (ECM), and the muscle cells can be provided suspended in the gel solution. The gel solution and suspended muscle cells can be seeded in one of the first and second muscle cells reservoirs 26, 28. The gel solution and suspended muscle cells can then migrate from one of the first and second muscle cells reservoirs 26, 28 to another one of the first and second muscle cells reservoirs 26, 28, via the neuromuscular junction chamber 30. After a certain period of time, i.e., after an incubation period, when the muscle cell reservoir fluid is provided as a gel solution, the muscle cells laden solution can polymerize into a hydrogel, and the muscle cells can remodel the hydrogel and self-assemble into a muscle tissue/fiber (also referred to as a muscle bundle) that is formed in the neuromuscular junction chamber 30, optionally between pillars when present, as will be discussed in further detail below. In some implementations, this configuration of the first and second muscle cells reservoirs 26, 28, neuromuscular junction chamber 30, neuronal cells channel 32 and neuronal cells inlet 24 can enable neuronal extensions to have a substantially clear path for growing in the neuronal cells channel 32 and reaching the neuromuscular junction chamber 30. In other words, this configuration of the first and second muscle cells reservoirs 26, 28, neuromuscular junction chamber 30, neuronal cells channel 32 and neuronal cells inlet 24 can enable establishing two types of flow: a first flow from the first muscle cells reservoir 26 to the second muscle cells reservoir 28 (or vice versa) via the neuromuscular junction chamber 30, and a second flow from the neuronal cells channel 32 into the neuromuscular junction chamber 30. The first flow can enable creating and sustaining the muscle tissue/fiber formed in the neuromuscular junction chamber 30, and treating the muscle tissue/fiber with any desired test substance, such as a chemical or a drug, among other functions. The second flow can enable guiding neuronal extensions towards the muscle tissue/fiber, so that innervation can occur to form the neuromuscular junction, and also to treat the neuronal cells with any desired test substance, such as a chemical or a drug, among other functions. In some implementations, the flow rate of the second flow can be lower than the flow rate of the first flow, or vice versa.

As briefly mentioned above, either one of the first and second muscle cells reservoirs 26, 28, or both, or the neuromuscular junction chamber 30 itself, is (are) further configured to receive a test substance therein, such that the muscle cells present in the neuromuscular junction chamber 30 and eventually forming the NMJ are exposed to such test substance. A test substance can be any type of substance that is desired to be tested to evaluate a response of the NMJ to that test substance, including toxins, antibodies, chemicals, biological substances, patient-derived fluids (plasma, serum, blood, urine, etc.), parasites, bacteria, viruses and/or cells. The test substance can take many forms, and can be for instance a liquid, a suspension, etc. The cell culture layer 22 can thus enable performing testing of substances, such as toxins, antibodies, chemicals, biological substances, drugs, patient-derived fluids (plasma, serum, blood, urine, etc.), parasites, bacteria, viruses and/or cells in selected compartments of the cell culture layer 22 such as the neuromuscular junction chamber 30 where the NMJ is formed. The test substance can thus include a biological material and/or a chemical material. When the test substance includes a biological material, it can any type of biological material for which it is desired to determine a response from the in vitro model of NMJ that can be obtained using the cell culture device 20 as described herein, such as a biological fluid or tissue from a patient, an antibody or antibody fragment, an antigen or antigen fragment, a toxin, an enzyme, DNA or RNA fragments, a virus, or bacteria, for instance. When the test substance includes a chemical material, it can any type of chemical material for which it is desired to determine a response from the in vitro model of NMJ that can be obtained using the cell culture device 20 as described herein, such as a drug, or any chemical compound. The in vitro model of NMJ can be used for example to test the potency of toxins and/or the toxicity of compounds such as chemical substances.

In some implementations, the test substance can be a toxin, and the toxin can include the Botulinum toxin. The Botulinum toxin has various applications, including in the pharmaceutical industry, the cosmetic industry and the food industry. In some implementations, the cell culture device as described herein can be used to test the neurotoxicity, potency and/or safety of the Botulinum toxin, for instance as part of quality control operations. Various products can also be tested to determine whether the Botulinum toxin is present or not. The above examples are given for exemplary purposes only, and it is to be understood that various other applications for testing the Botulinum toxin are within the scope of the present description.

The in vitro model of NMJ that can be obtained using the cell culture device 20 as described herein can be used to analyse the effect of a test substance on the functionality of the NMJ by measuring a functionality parameter related to the NMJ. Examples of a functionality parameter can include, without being limited to, at least one of a contraction force from the muscle cells, a contraction duration of the muscle cells, a neuronal cells viability, a muscle cells viability, a neuronal cells survival rate, a muscle cells survival rate, a calcium signalling indicator, and an electrical signal from the neuronal cells or from the muscle cells, for instance. As mentioned above, the test substance can include a biological material from a patient, and/or a chemical material.

For instance, in an example implementation of the cell culture device 20 that is used to develop an in vitro model of NMJ, a biological material obtained from a patient can be tested using the in vitro model of NMJ. The in vitro model of NMJ can be used for example to test serum from patients with an autoimmune disease, such as Myasthenia Gravis, to evaluate the presence of one or more specific antibodies or compounds that can affect the function of the NMJ. The biological material can be withdrawn, or taken, from the patient following the administration of a given drug to the patient. In such scenarios, the biological material withdrawn from the patient can contain a patient-specific substance such as an antibody, a metabolite, or an active ingredient of the drug, for instance, resulting in a given combination of this patient-specific substance with this specific patient. This given combination can subsequently be tested on the NMJ, for instance to evaluate a response of the NMJ to this given combination. Alternatively, the biological material can be withdrawn, or taken, without the patient having previously been administered a drug, and this biological material can be tested on the NMJ to evaluate a response of the NMJ thereto. In some implementations, it can be desired to compare the response of the NMJ to the given combination of the patient-specific substance with this specific patient, to the response of the NMJ to the biological material withdrawn from the same patient but without the patient having previously been administered a drug. In accordance with this implementation, it can be possible to determine whether the drug administered to the patient has an impact on the NMJ, such as an impact of the function of the NMJ, which in turn, can contribute to determine whether that drug can have a therapeutic benefit for the patient. This scheme can be considered similar to a cross-over trial design, involving the same patient from which two types of biological materials are successively tested on the in vitro model of a NMJ.

In another example implementation of the cell culture device 20 that is used to develop an in vitro model of a NMJ, a given drug can be administered to a first group of patients (which can include one or more patients), while a second group of patients (which can include one or more patients), do not receive the given drug. In such scenarios, a corresponding biological material can be withdrawn, or taken, from the one or more patients of the first group of patients, and a corresponding biological material can be withdrawn, or taken, from the one or more patients of the second group of patients. The effects of the corresponding biological materials of the first group of patients on the NMJ can then be evaluated, and the effects of the corresponding biological materials of the second group of patients on the NMJ can be evaluated parallelly. The respective effects of the corresponding biological materials of the first group of patients and the second group of patients can then be compared, similarly to a parallel trial design.

In yet another example implementation, the cell culture device 20 can be used as a diagnostic tool to determine if a patient suffers from a given condition, such as a disease, e.g., an autoimmune disease or an alloimmune disease. In such scenarios, a sample of biological material can be withdrawn, or taken, from the patient, and the biological material can be tested on the in vitro model of NMJ obtained by using the cell culture device 20 to evaluate the impact of the biological material on the NMJ. Following the addition of the biological material from the patient to the vitro model of NMJ, the NMJ function can be assessed to determine if the biological material has an impact on the NMJ function. Examples of endpoints that can be evaluated to assess NMJ function can include, but are not limited to, the extent and/or duration of muscle contraction after subjecting the NMJ to a neuronal stimulus, and the determination of whether the addition of the biological material from the patient to the vitro model of NMJ has caused neuronal degeneration. For instance, in certain types of autoimmune or alloimmune diseases, the body can produce antibodies that impair the function of the NMJ. By enabling testing of the impact of the biological material from the patient that is suspected of suffering from an autoimmune disease or an alloimmune disease on NMJ function, the in vitro model of NMJ obtained by using the cell culture device 20 described herein can be used to evaluate if these antibodies have an effect of the NMJ. If this is the case, then it can be determined that the patient may have a given condition and/or that a given drug may be useful in the treatment of the patient's condition.

It is to be understood that the above scenario is described as an example of application where the cell culture device 20 and the resulting in vitro model of NMJ can be used as a diagnostic tool, and that the cell culture device 20 and the resulting in vitro model of NMJ can be used to diagnose other types of diseases or conditions involving the NMJ.

Turning back to the Figures, the neuronal cells inlet 24, and the first and second muscle cells reservoirs 26, 28 shown in FIG. 3 are open to the atmosphere, i.e., are open-top, to enable the introduction of the various fluids, cells and optionally test substances in selected compartments of the cell culture layer 22. The neuronal cells inlet 24 and the first and second muscle cells reservoirs 26, 28 are thus through-holes extending across an entire thickness of the cell culture layer 22. Once the cell culture layer 22 is deposited onto a cell culture layer receiving surface of a cell culture plate, a cell culture dish or a microscope slide, the cell culture layer receiving surface can act as the back wall of the neuronal cells inlet 24 and the first and second muscle cells reservoirs 26, 28, such that fluids introduced in the neuronal cells inlet 24 and the first and second muscle cells reservoirs 26, 28 can remain therein. In alternative implementations, at least one of the neuronal cells inlet 24 and the first and second muscle cells reservoirs 26, 28 can include a back wall provided by the cell culture layer 22 itself, and thus not extend across the entire thickness of the cell culture layer 22.

In some implementations, the first and second muscle cells reservoirs 26, 28 can each have a diameter ranging from about 2 mm to about 6 mm. In some implementations, the neuronal cells inlet 24 can have a diameter ranging from about 2 mm to 10 mm. In some implementations, the cell culture layer 22 can have a diameter ranging from about 8 mm to about 30 mm. These dimensions are given for example only, in a scenario where the cell culture layer 24 is configured to be inserted in a cell culture dish, and it is to be understood that other dimensions of the compartments mentioned above and of the cell culture layer 24 are of course possible. For instance, when the cell culture layer is inserted into a well of a multi-well cell culture plate, the dimensions of the cell culture layer can be adapted such that the cell culture layer can fit within the a given well of the multi-well cell culture plate.

In the implementations shown in FIGS. 1-8, 10, 11, 13-23, the neuromuscular junction chamber 30 includes a first pillar 40 and a second pillar 42 provided in a space-apart relationship relative to one another. The first pillar 40 is provided in closer proximity to the first muscle cells reservoir 26 compared to the second muscle cells reservoir 28, and the second pillar 42 is provided in closer proximity to the second muscle cells reservoir 28 compared to the first muscle cells reservoir 26. The first and second pillars 40, 42 can serve as anchoring points to enable the assembly of muscle cells therebetween and formation of a muscle fibers and/or muscle tissue attached thereto. The shape and size of the pillars 40, 42 can vary. For instance, the pillars can have a substantially cylindrical shape with a circular cross section, thereby forming a right circular cylinder. In other implementations, and as shown in FIG. 20, either one, or both, of the pillars can have an elliptical cross section, thereby forming an elliptic cylinder. In other implementations, either one, or both, of the pillars can form an oblique cylinder. Other configurations and shapes of the pillars than those illustrated are also possible, and any physical structure that can enable anchoring the muscle fibers can be suitable. For instance, in some implementations, either one of the first pillar 40 and the second pillar 42, or both, can include a wire. The wire can be a flexible wire, that can be deflectable in response to a movement of the muscle cells of the NMJ, such as a contraction of the muscle cells. The wire can be made of a metal or a polymer, or any other suitable material.

Figure 9:
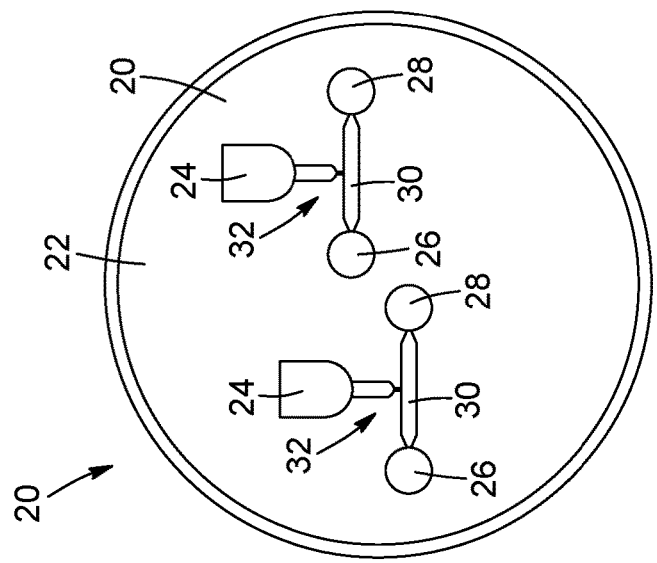
FIG. 9 is a bottom view of a cell culture device that includes two neuromuscular junction preparation units, each neuromuscular junction preparation unit including a neuronal cells channel shaped as a cup and a neuromuscular junction chamber.
Figure 12:
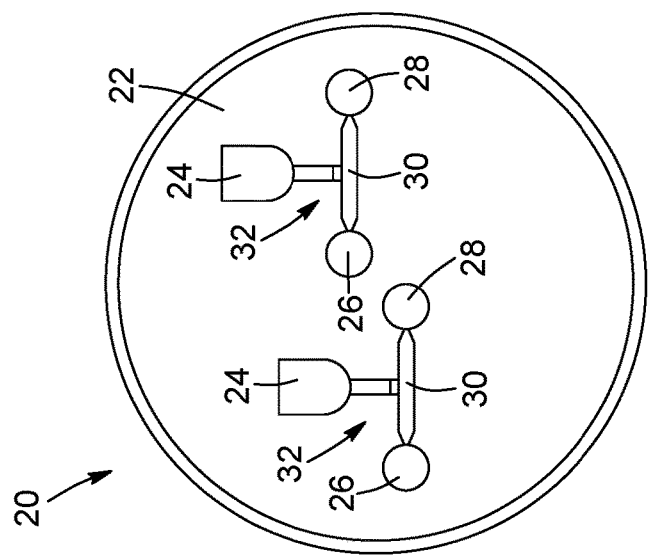
FIG. 12 is a bottom view of a cell culture device that includes two neuromuscular junction preparation units, each neuromuscular junction preparation unit including a neuronal cells channel having an abutment, and a neuromuscular junction chamber.
Figure 13:
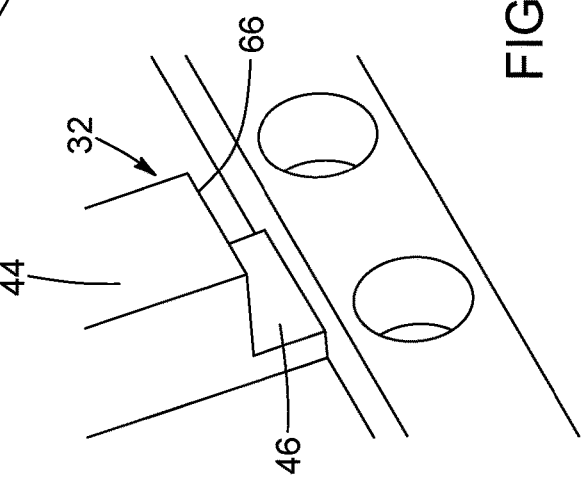
FIG. 13 is an enlarged front perspective view of a mold for producing the cell culture device shown in FIG. 11.
Figure 11:
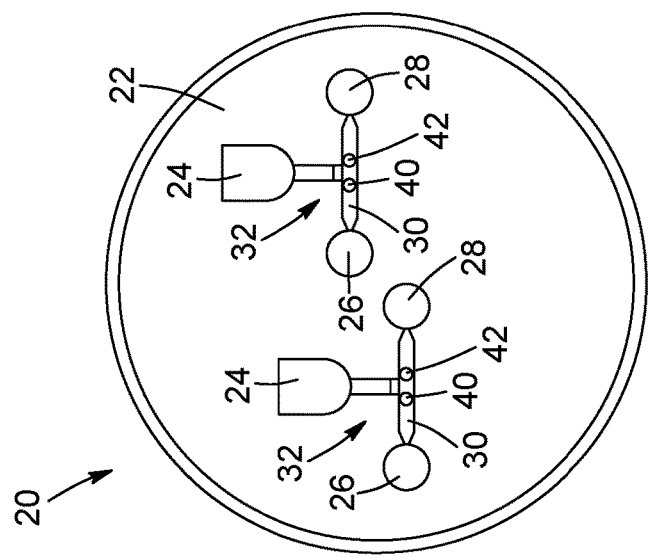
FIG. 11 is a bottom view of a cell culture device that includes two neuromuscular junction preparation units, each neuromuscular junction preparation unit including a neuronal cells channel having an abutment, and a neuromuscular junction chamber that includes two pillars.

In other implementations and as shown in FIGS. 9 and 12 for instance, the pillars can be omitted.

In some implementations, such as in the implementations illustrated in FIGS. 1-7, the pillars 40, 42 can have a diameter ranging from about 0.5 mm to about 10 mm. Other dimensions of the pillars are also possible, for instance depending on the intended use of the cell culture layer 22 and on whether the cell culture layer 22 is intended to be used with a cell culture plate, a cell culture dish or a microscope slide. The distance between the first and second pillars 40, 42 can vary depending on the desired length of the muscle fibers extending therebetween. On the other hand, the distance between the first and second pillars 40, 42 may be kept within a certain range to ensure formation of muscle fibers that are viable and thick enough, i.e., not too thin, and thus to favour growth of the muscle fibers. The pillars 40, 42 can be configured so as to remain in position when subjected to a force, i.e., the pillars can be configured so as to not deflect when subjected to a given force. Alternatively, the pillars 40, 42 can be configured to deflect when subjected to a given force.

In some implementations, when at least one of the first and second pillars 40, 42 is a deflectable pillar, such as a deflectable wire or another type of deflectable pillar, the extent of the deflection and/or the duration of the deflection of the at least one of the first and second pillars 40, 42 can be assessed in response to a contraction of the muscle cells of the NMJ, which can be initiated for instance following an electrical, chemical or optical stimulation. With such a configuration of the at least one of the first and second pillars 40, 42, the cell culture device 20 can be used to test various tests substances, e.g., a biological material or a chemical material, with respect to their impact on the functionality of the NMJ, i.e., on a functionality parameter of the NMJ. In turn, knowing the impact of the test substance on the functionality of the NMJ can contribute to the determination of whether a test substance has a desired effect on the NMJ, or to the contrary, results in an undesired effect on the NMJ.

Neuronal Cells Channel

More details regarding the neuronal cells channel 32 shown in FIGS. 1-23 will now be provided.

The neuronal cells channel 32 extends between the neuronal cells inlet 24 and the neuromuscular junction chamber 30 and is in fluid communication therewith. In some implementations and as shown in FIGS. 1-23, the neuronal cells channel 32 can join the neuromuscular junction chamber 30 at a central region of the neuromuscular junction chamber 30. In some implementations, the neuronal cells channel 32 can join the neuromuscular junction chamber 30 at a location that is equidistant from the first muscle cells reservoir 26 and from the second muscle cells reservoir 28. When pillars are present in the neuromuscular junction chamber 30, such as pillars 40, 42, the neuronal cells channel 32 can join the neuromuscular junction chamber 30 at a central region between the two pillars of the neuromuscular junction chamber 30. In some implementations, the neuronal cells channel 32 can join the neuromuscular junction chamber 30 at a location that is equidistant from a first one of the pillars and from a second one of the pillars. For instance, in FIG. 1, a centerline of the neuronal cells channel 32 joins the neuromuscular junction chamber 30 at a distance from the first pillar 40 that is substantially equal to the distance from the second pillar 42. Alternatively, the neuronal cells channel 32 can join the neuromuscular junction chamber 30 at another location than at a central region of the neuromuscular junction chamber 30, i.e., closer to one of the first and second muscle cells reservoir 26, 28.

Figure 2:
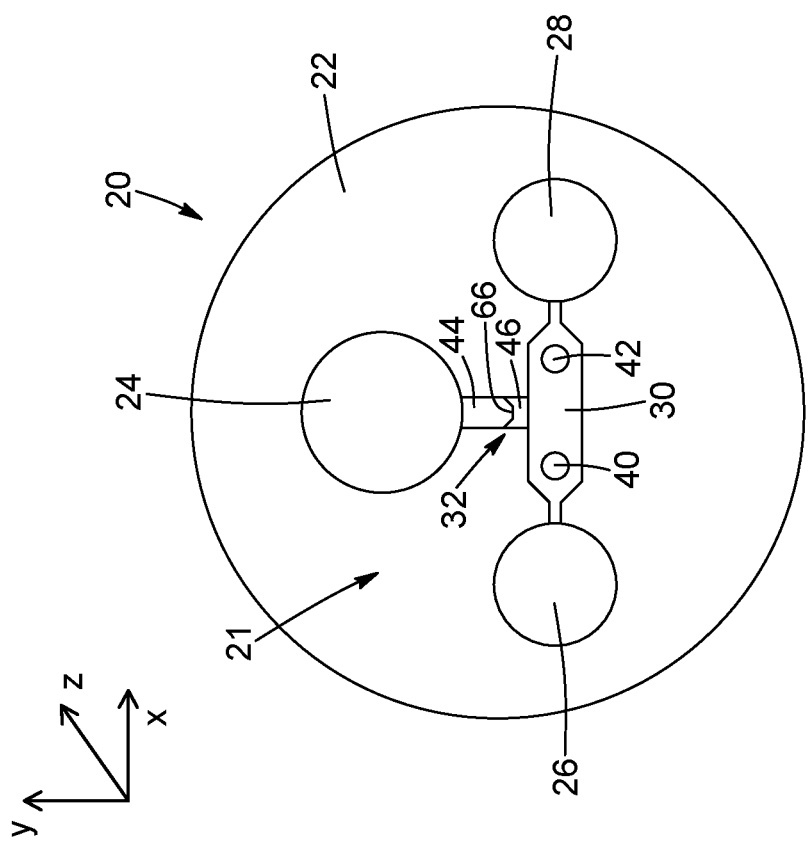
FIG. 2 is a front view of the cell culture device of FIG. 1.
Figure 5:
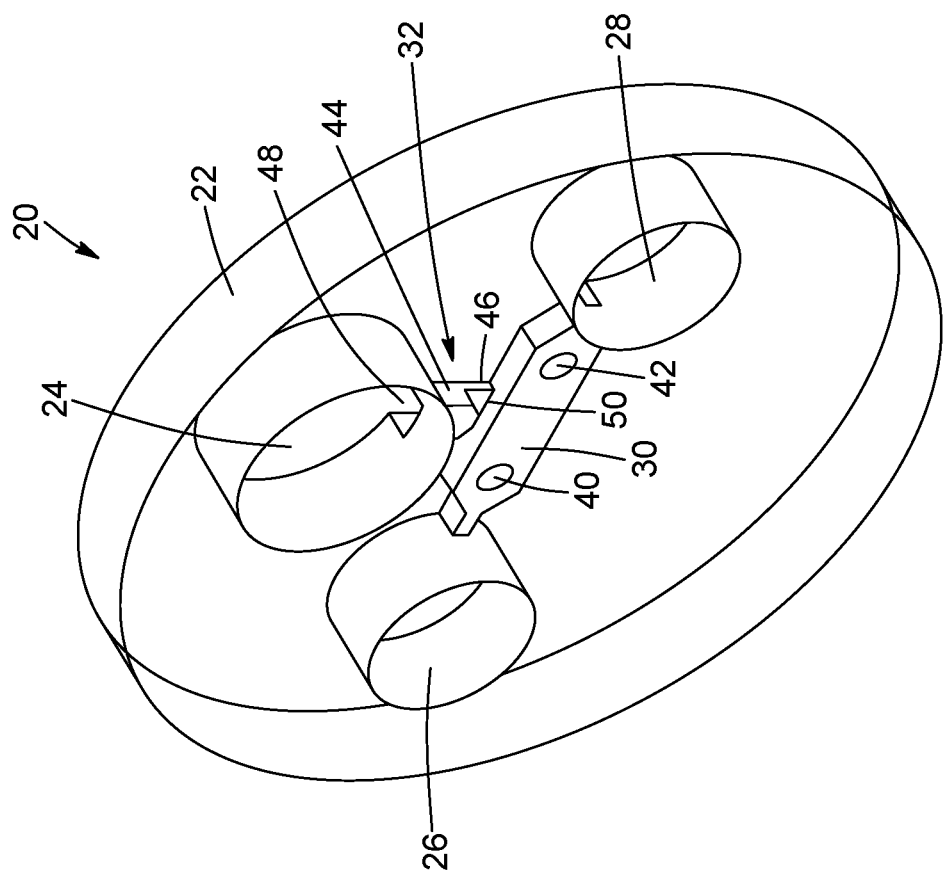
FIG. 5 is another front perspective view of the cell culture device of FIG. 1.
Figure 4:
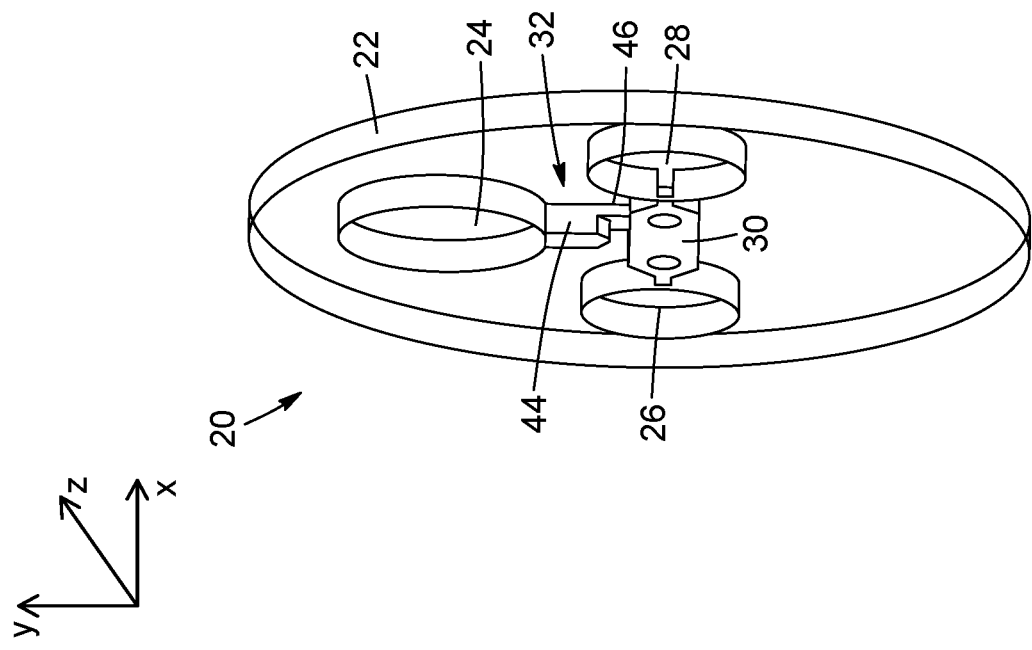
FIG. 4 is a front perspective view of the cell culture device of FIG. 1.

The neuronal cells channel 32 includes a first portion 44 having a first portion cross-section, and a second portion 46, provided downstream of the first portion 44 and having a second portion cross-section. As seen in FIGS. 2 and 5, the neuronal cells channel 32 is enclosed within the cell culture layer 22, with a first end 48 of the neuronal cells channel 32 opening into the neuronal cells inlet 24 and a second end 50 of the neuronal cells channel 32 opening into the neuromuscular junction chamber 30. It is to be understood that in alternative implementations, the neuronal cells channel 32 can be configured as an open-top neuronal cells channel.

The first portion 44 of the neuronal cells channel 32 includes first portion sidewalls 52, a first portion front wall 54 and a first portion back wall (not shown in FIG. 3B). The second portion 46 of the neuronal cells channel 32 comprises second portion sidewalls 56, a second portion front wall 58 and a second portion back wall (not shown in FIG. 3B). In some implementations, the first portion back wall and the second portion back wall can be provided by the cell culture layer receiving surface of the cell culture dish, cell culture plate or microscopic slide with which the cell culture layer 22 is used. This type of implementations is shown in FIGS. 1-7, illustrating that the back of the cell culture layer 22 is open when not in contact with the cell culture layer receiving surface of the cell culture dish, cell culture plate or microscopic slide with which the cell culture layer 22 is used. In such implementations, the cell culture layer receiving surface thus provides the confinement of the neuronal cells channel 32 along this plane. In other implementations, the first portion back wall and the second portion back wall can be integral with the cell culture layer 22, i.e., can form part of the cell culture layer 22.

Figure 7:
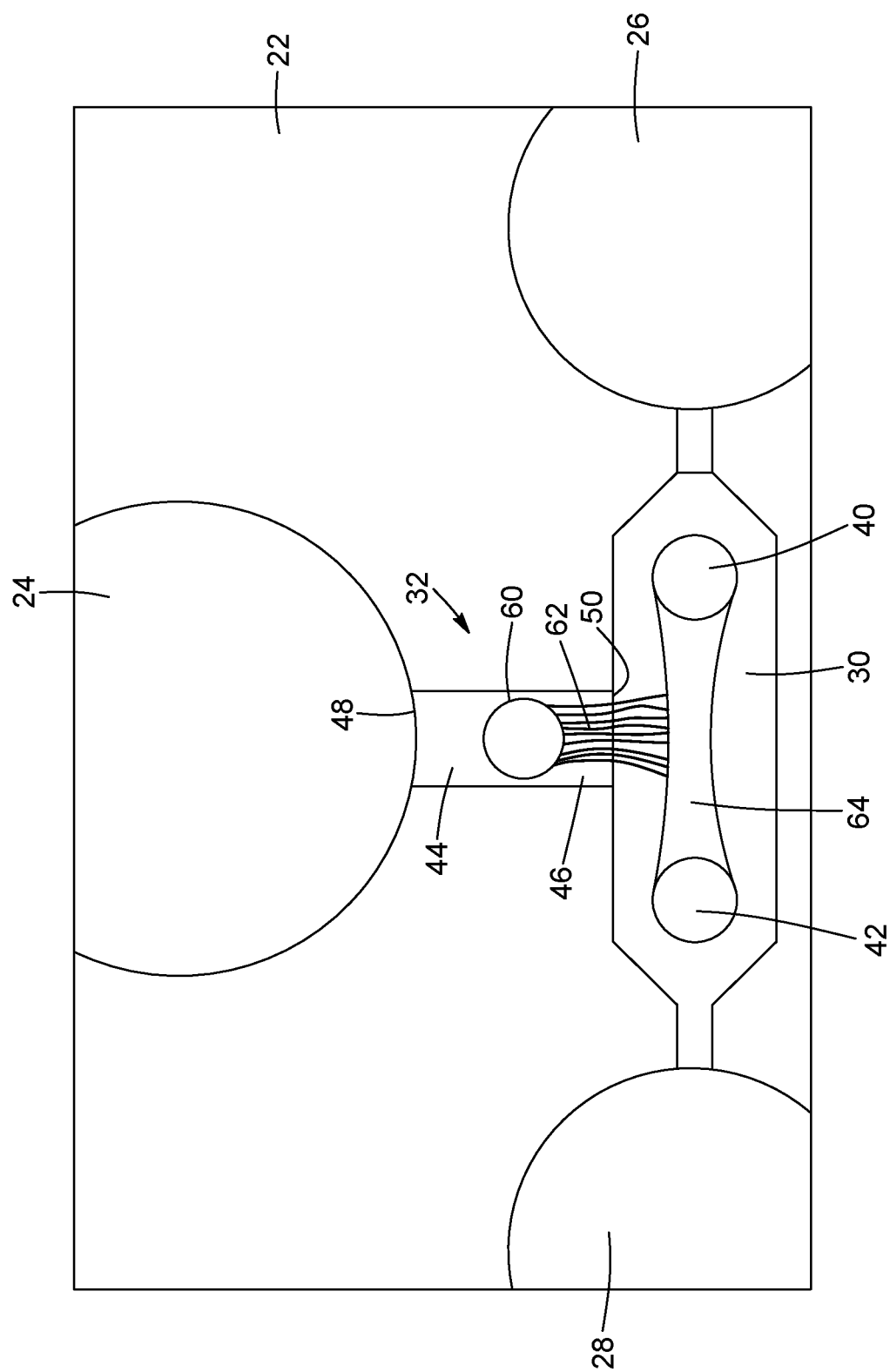
FIG. 7 is an enlarged bottom view of a portion of a cell culture device, showing a portion of a neuronal cells inlet, a portion of a first muscle cells reservoir, a portion of a second muscle cells reservoir, a neuromuscular junction chamber, a neuronal cells channel, a neurosphere and muscle cells.

When the cell culture layer 22 is configured for use with three-dimensional neuronal assemblies, or clusters, of neuronal cells such as neurospheres, spheroids, neural aggregates, or neuro-organoids, the first portion 44 of the neuronal cells channel 32 can be sized and configured to receive the neurospheres, neural aggregates, or neuro-organoids therein. For sake of simplicity, the three-dimensional neuronal assemblies will collectively be referred to as "neurospheres" throughout the present description. It is thus to be understood that when referring to a neurosphere herein, it is meant to include all types of three-dimensional neuronal assemblies. In other words, the first portion cross-section of the first portion 44 of the neuronal cells channel 32 is chosen to be at least large enough to receive one or more neurospheres therein. In that regard, the first portion cross-section can be considered as corresponding to the transversal surface area delimited by the first portion sidewalls 52, the first portion front wall 54 and the first portion back wall. The one or more neurospheres can thus be introduced in the neuronal cells inlet 24, and can migrate toward the neuronal cells channel 32 where the portion of the neurosphere that contains the neuronal cell bodies will remain in the first portion 44 of the neuronal cells channel 32. FIG. 7 illustrates an example of a first portion 44 of a neuronal cells channel 32 that is sized to receive a schematically represented neurosphere 60 therein.

Although not shown in the figures, in some implementations, the NMJ preparation unit can include a plurality of neuronal cells channel 32 provided side-by-side and in a spaced-apart relationship with regard to each other, each one of the neuronal cells channels 32 having a respective second end 50 that opens into the neuromuscular junction chamber 30.

In order to retain the portion of the neurosphere that contains the neuronal cell bodies within the first portion 44 of the neuronal cells channel 32, the second portion cross-section is smaller than the first portion cross-section, the size being determined to prevent entry of the portion of the neurosphere that contains neuronal cell bodies into the second portion 46, i.e., to prevent entry of the neuronal cell bodies in the second portion 46. The second portion 46 is further sized to house axons and enable the axons to extend away from the neuronal cell bodies, directing the axons toward the neuromuscular junction chamber 30 so as to reach the muscle cells cultured in the neuromuscular junction chamber 30. FIG. 7 illustrates an example of axons 62 extending from a neurosphere 60 located in the first portion 44 of the neuronal cells channel 32, the axons 62 extending into the second portion 46 of the neuronal cells channel 32 and out to the neuromuscular junction chamber 30 to reach muscle cells 64 extending between the first pillar 40 and the second pillar 42. The second portion cross-section can be considered as corresponding to the transversal surface area delimited by the second portion sidewalls 56, the second portion front wall 58 and the second portion back wall. The reduced second portion cross-section compared to the first portion cross-section can be achieved in various ways, which will be described in more detail below.

With reference to FIGS. 1-7, 22 and 23, the neuronal cells channel 32 can have a substantially constant channel width w (shown in FIG. 3B) along the x-axis throughout its length determined along the y-axis. In other words, the first portion sidewalls 52 can transition to the second portion sidewalls 56 substantially linearly, such that the neuronal cells channel 32 has a channel width w that is substantially the same between the first portion 44 and the second portion 46. The constant channel width w of the neuronal cells channel 32 can be the result of the neuronal cells channel 32 being shaped as a rectangular prism having a substantially constant width along the x-axis throughout its length determined along the y-axis of the cell culture layer 22, or of the neuronal cells channel 32 being shaped as a cylinder having a substantially constant diameter along the x-axis throughout its length determined along the y-axis of the cell culture layer 22. The width can be chosen to be large enough for receiving one or more neurospheres therein, while being small enough to contribute to stabilizing the one or more neurospheres therein. For example, the channel width, or diameter, of the first portion 44 can be determined so as to obtain a given ratio between the channel width of the first portion 44 and the width of the neurosphere. For instance, in some implementations, the ratio of the neurosphere width, or diameter, relative to the channel width can range from about 1.25 to about 2. This range of ratios is given as an example only, as the three-dimensional neuronal assemblies can take various forms and sizes, and the size of the neuronal cells channel 32 can be adapted accordingly. One objective of the sizing of the neuronal cells channel 32 is to enable stabilization of one or more three-dimensional neuronal assemblies contained therein, while enabling efficient cell culture medium flow between the neuronal cells channel 32 and the neuromuscular junction chamber 30. In addition, the first portion 44 is thus sized and configured to house at least one neurosphere therein and prevent the cell bodies of the neurosphere to travel downstream into the second portion 46 of the neuronal cells channel 32.

As mentioned above, the second portion 46 of the neuronal cells channel 32 has a second portion cross section that is smaller than the first portion cross-section of the first portion 44 of the neuronal cells channel 32. In FIGS. 1-7, the reduction in the cross section is achieved by a reduction in the channel height h of the second portion 46 compared to the channel height h of the first portion 44. In order to do so, the second portion front wall 58 is located inwardly, i.e., toward the second back wall along the z-axis, compared to the first portion front wall 54. This offset of the second portion front wall 58 relative to the first portion front wall 54 defines an abutment wall 66 within the neuronal cells channel 32. The location of the abutment wall 66 can be considered as the location of the transition from the first portion 44 to the second portion 46. The abutment wall 66 can serve as a surface against which the one or more neurospheres can rest or lean. The extent of the reduction in the channel height h in the second portion 46 of the neuronal cells channel 32 can be determined such that the one or more neurospheres are prevented to travel downstream into the second portion 46, while enabling the axons of the one or more neurospheres to extend in the second portion 46 to reach the neuromuscular junction chamber 30 through the second end 50 of the neuronal cells channel 32.

In the implementation shown in FIGS. 1-7, the abutment wall 66 is shaped so as to converge inwardly toward a centerline of the neuronal cells channel 32, along the x-axis. The convergence of the abutment wall 66 toward the centerline of the neuronal cells channel 32 can contribute to stabilizing the one or more neurospheres in the first portion 44 of the neuronal cells channel 32. As shown in FIGS. 3A and 3B, the convergence of the abutment wall 66 toward the centerline of the neuronal cells channel 32 can be achieved by a succession of a plurality of substantially straight planes oriented toward said centerline. Alternatively, in some implementations, the convergence of the abutment wall 66 toward the centerline of the neuronal cells channel 32 can be achieved by a curved abutment wall, i.e., a concave abutment wall (see for instance FIGS. 8-10). In yet other implementations, the abutment wall 66 can be substantially flat (see for instance FIGS. 11-16). It is to be understood that the abutment wall 66, whether the abutment wall 66 is substantially flat, includes a plurality of substantially straight planes oriented toward the centerline of the neuronal cells channel 32, or is concave, does not include an opening but is rather continuous, i.e., the abutment wall 66 is apertureless.

In other words, the reduction in size of the channel height h from the first portion 44 to the second portion 46 can be such that at a certain location along the length, i.e., along the y-axis, of the neuronal cells channel 32, the cross section of the neuronal cells channel 32 becomes too small for the cell bodies of the one or more neurosphere to travel further down along the y-axis of the neuronal cells channel 32, such that the cell bodies of the one or more neurosphere are retained upstream of the second portion 46. In some implementations, the ratio between the channel height h in the first portion 44 relative to the channel height h in the second portion 46 can range from about 2 to about 12, from about 3 to about 9, or from between about 3 and about 7. In some implementations, the channel height h in the first portion 44 can range from about 0.02 mm to about 1.2 mm, and the channel height h in the second portion 46 can range from about 0.01 mm to about 1 mm. In an example implementation, the channel height h in the first portion 44 can range from about 0.5 mm to about 1 mm, and the channel height h in the second portion 46 can range from about 0.01 mm to about 0.5 mm. It is to be understood that these dimensions are given for exemplary purposes only, and that in other implementations, the dimensions of the first portion 44 and the second portion 46 of the neuronal cells channel 32 can be higher or lower depending on the intended use of the cell culture device.

Figure 10:
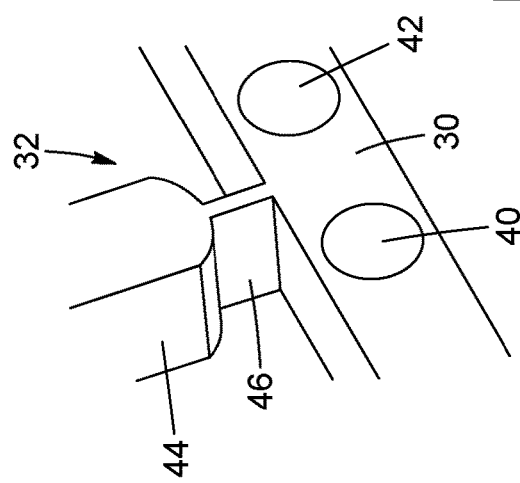
FIG. 10 is an enlarged front perspective view of a mold for producing the cell culture device shown in FIG. 8.
Figure 8:
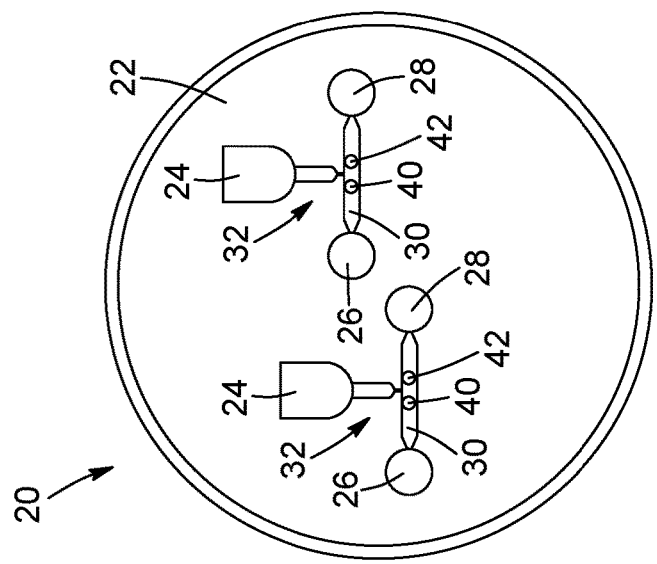
FIG. 8 is a bottom view of a cell culture device that includes two neuromuscular junction preparation units, each neuromuscular junction preparation unit including a neuronal cells channel shaped as a cup and a neuromuscular junction chamber that includes two pillars.

In alternative implementations, the reduced second portion cross section compared to the first portion cross section, in addition to the reduction in the channel height h, can be further achieved by a reduction in the channel width w, such as shown in FIGS. 8-10. In such implementations, the channel width w can thus be larger in the first portion 44 compared to the channel width w in the second portion 46. The transition from the first portion 44 to the second portion 46 can be achieved for instance by a step change, an inclined wall or a curved wall. When the transition from the first portion 44 to the second portion 46 is achieved for instance by a step change, the step change can include one or more rounded edges.

In the implementations shown in FIGS. 1-7, 11-16 and 19-23, the reduction in the channel height h from the first portion 44 to the second portion 46 is achieved by the second portion front wall 58 being provided inwardly from the second portion back wall 54 along the z-axis, i.e., closer to the second portion back wall compared to the location of the first portion front wall 54 relative to the first portion back wall. In some implementations, the reduction in the channel height h can also be further achieved by the second portion back wall being provided inwardly along the z-axis, toward a centerline of the neuronal cells channel 32. This type of implementations can be achieved when the second portion back wall is provided by the cell culture layer 22 itself, rather than being provided by the cell culture layer receiving surface of a cell culture plate, a cell culture dish or a microscope slide. In yet other implementations, the reduction in the channel height h can be solely achieved by the second portion back wall being provided inwardly along the z-axis, toward a centerline of the neuronal cells channel 32.

When the abutment wall 66 is concave, the combination of the first portion sidewalls 52 with the abutment wall 66 can form a cup, such as shown in FIGS. 8-10. The size and configuration of the cup can be adapted in accordance with the size and shape of the neurosphere that is intended to be received in the cup, so as to match the size and shape of the neurosphere. For instance, for a neurosphere that is substantially circular, the first portion, i.e., the cup, can be sized such that the cell bodies of the neurosphere leans lightly against the abutment wall 66, with the axons extending within the second portion 46, downstream of the first portion 44.

Electrode Layer

In some implementations, the cell culture device 20 can further include an electrode or a group of electrodes. The electrode, or group of electrodes, can be provided so as to be in contact, either direct or indirect, i.e., in electrical communication, with the neurons, the muscle cells and/or the neuromuscular junction formed in the neuromuscular junction chamber 30, and/or the axons, i.e., the neuronal extensions, extending within the neuronal cells channel 32. The electrode or group of electrodes can take the form of an electrode layer that can be placed underneath the cell culture layer 22, or superposed to the cell culture layer 22 to enable electrical communication with the neuronal cells and/or the muscle cells. Alternatively, the electrode or the group of electrodes can be provided in proximity of the cell culture layer 22, i.e., without necessarily be placed underneath or superposed thereto. When the electrode layer is provided in proximity of the cells, the distance between the electrode(s) of the electrode layer and the cells can be in the range of micrometers or millimeters, for instance. In yet other implementations, the electrodes can be provided so as to be inserted in the cultured material, such as the neuronal cells growing in the neuronal cell channel 32 and/or the neuronal cells and the muscle cells growing the neuromuscular junction chamber 30. In such implementations, the electrodes can thus be provided within one or more compartments of a NMJ preparation unit, for instance on a top surface or a bottom surface of the one or more compartments of the NMJ preparation unit, and/or on the sidewalls of one or more compartments of the NMJ preparation unit.

Figure 34:
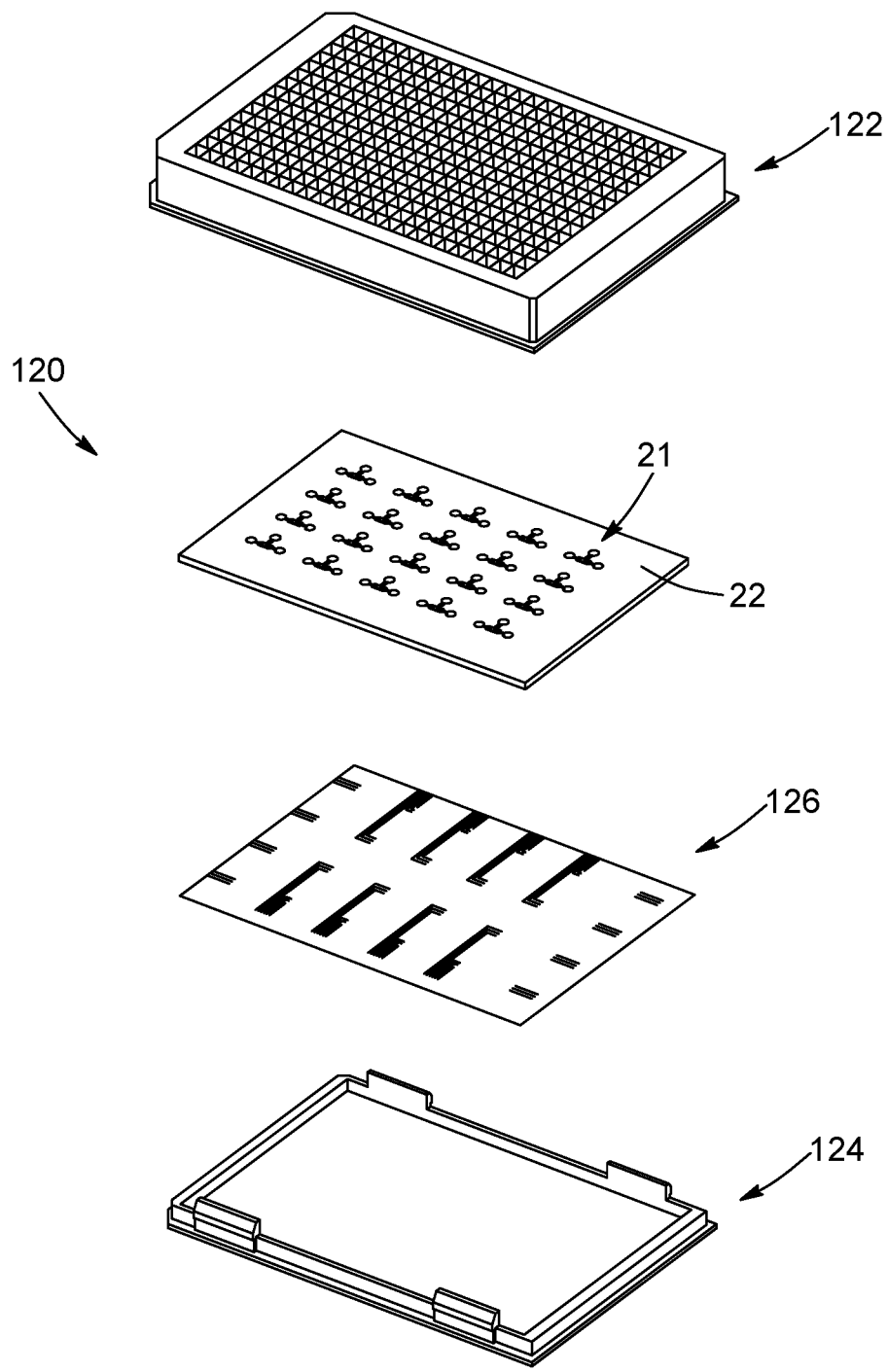
FIG. 34 is an exploded perspective view of a cell culture layer in combination with a cell culture plate that includes a multi-grid layer and a base layer, and an electrode layer provided underneath the cell culture layer.

In some implementations, the electrode layer can be placed onto a cell culture layer receiving surface of a cell culture plate, a cell culture dish or a microscope slide, for instance, with the cell culture layer 22 being placed onto the electrode layer. FIG. 34 illustrates an example of a cell culture device 120 that includes a multi-well grid layer 122 and a base layer 124, with a cell culture layer 22 and an electrode layer 126 provided between the multi-well grid layer 122 and the base layer 124. Alternatively, the cell culture layer 20 can be received onto a cell culture layer receiving surface of a cell culture plate, a cell culture dish or a microscope slide, for instance, and the electrode layer can be placed onto the cell culture layer 20. In yet other implementations, a first electrode layer can be placed onto a cell culture layer receiving surface of a cell culture plate, a cell culture dish or a microscope slide, for instance, with the cell culture layer 22 being placed onto the electrode layer, and a second electrode layer can be placed onto the cell culture layer 20. In yet other implementations, the electrode or group of electrodes can be integrated in the cell culture layer 20. In yet other implementations, the electrodes can be provided as spikes or needles to facilitate contact with the neuronal cells growing in the neuronal cell channel 32 and/or the neuronal cells and the muscle cells growing the neuromuscular junction chamber 30.

In some implementations, multiple electrode layers can be provided according to a combination of any of the locations described above.

It is to be understood that the electrode layer can be provided in proximity of the in vitro model of NMJ, either directly or indirectly in contact therewith. The proximity of the electrode layer with the neuronal cells growing in the neuronal cell channel 32 and/or the neuromuscular junction chamber 30 can facilitate providing electrical stimulation to the NMJ and recording electrical signals from the NMJ, which can enable measuring a response from the muscle cells, such as by contraction, to stimulation of the neuronal cells, or a response from the neuronal cells to stimulation of the muscle cells. The combination of the electrode(s) and the cell culture layer 22 can thus enable the determination of the neuronal function and the muscular function of the in vitro model of NMJ, for instance in response to electrical impulses or calcium signaling, and of the overall function of the NMJ.

In some implementations, the same electrode can be configurable to sequentially perform different actions. For instance, the actions can be any of collecting, recording, measuring, and/or detecting a response of the cells to stimulation. For instance, the electrode can be configured to collect a signal at a given timepoint, and at a subsequent timepoint, the electrode can be configured to provide an electrical signal. In some implementations, the electrode can be configured to detect an optical signal or an electrical signal.

In some implementations, the distribution of the electrodes over the surface area of the electrode layer can be such that it follows an orientation of the neuronal extensions growing in the neuronal cells channel 32, or an orientation of the muscle cells extending between the first and second pillars 40, 42, instead of the electrodes being provided randomly across the cell culture layer 22. The distribution of the electrodes can also be such that it includes a first group of electrodes following an orientation of the neuronal extensions growing in the neuronal cells channel 32, and a second group of electrodes following an orientation of the muscle cells extending between the first and second pillars 40, 42. Providing the electrodes in such a configuration can enable obtaining electrodes in an organized fashion which in turn, can enable to better target the function of the electrodes, for instance with respect to the stimulation of the neuronal cells or the muscle cells, or with respect to the detection of a signal from the neuronal cells or from the muscle cells.

In some implementations, the electrode can comprise at least one metallic electrode, at least one metal oxide electrode, at least one carbon electrode, a multi-electrode array, and/or at least one field effect transistor detectors.

In some implementations, the cell culture device 20 can include any other types of sensors that can stimulate cells or measure responses of cells to stimulation, e.g., stimulating neuronal cells and/or muscle cells, measuring a response from the neuronal cells and/or muscle cells to stimulation, providing an output and/or receiving an input. Examples of sensors can include optical sensors or optical transducers, chemical sensors, and electrical sensors or electrical transducers, for instance. The sensors can be provided according to any of the implementations described above with respect to the electrodes.

Thus, the cell culture device can include any type of electrode and/or sensor that is in contact with the neuronal cells growing in the neuronal cell channel 32 and/or the neuronal cells and the muscle cells growing the neuromuscular junction chamber 30, and that is configured to provide an output to the neuronal cells and/or the muscle cells, and/or receiving an output from the neuronal cells and/or the muscle cells. The output provided or the output received can be any one of a chemical output, an electrical output and a physical output.

In some implementations, the cell culture device 20 can include an electrode set provided proximate to the in vitro model of NMJ. The electrode set can include at least one electrode configured to collect an electric signal associated with at least a portion or at least one compartment of the in vitro model of NMJ. The electrode set can take the form of an electrode layer as described above, or can take a different form. The electrode set can include more or more electrodes. The electrodes can enable providing electrical read-outs comprising one or more of potential recordings, impedance spectroscopy, voltammetry and amperometry.

In some implementations, the cell culture device 20 can include an electronic device in ohmic connection with the electrode described above. The electronic device can include for instance a sensing device or a stimulating device, and can be configured for providing electrical read-outs comprising one or more of potential recordings, impedance spectroscopy, voltammetry and amperometry. The electronic device can be located for instance within the reservoir of a cell culture dish or within a well of a cell culture plate, or be provided in proximity thereof.

Alternative Implementations of the Neuronal Cells Channel

Alternative implementations of the configuration of the neuronal cells channel will now be described in further detail.

As mentioned above, when the abutment wall 66 is concave, the combination of the first portion sidewalls 52 and the abutment wall 66 can form a cup. FIG. 10 illustrates an example implementation of a first portion 44 that is shaped as a cup. Although not shown in FIG. 10, it is to be understood that the second portion 46 can include a second portion front wall or a second portion back wall, or both, that is provided inwardly toward a centerline of the neuronal cells channel 32 along the z-axis, such that the second portion 46 has a reduced channel height h compared to the channel height of the first portion 44.

In some implementations, the first portion 44 can include a frustoconical converging portion. In other implementations, the first portion 44 can include a frustopyramidal converging portion. In such implementations, the transition from the first portion 44 to the second portion 46 can be considered to be located where the cross section of the neuronal cells channel 32 become sufficiently small to prevent the one or more neurospheres to continue traveling further toward the neuromuscular junction chamber 30.

Figure 15:
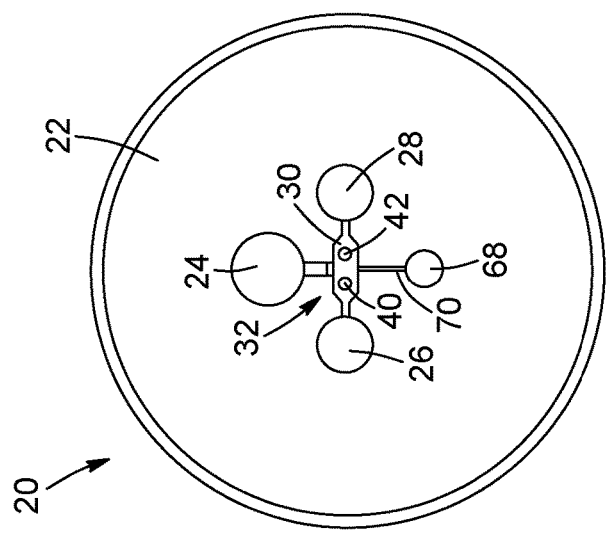
FIG. 15 is a bottom view of a cell culture device that includes a cell culture layer having a neuronal cells inlet, a first muscle cells reservoir, a second muscle cells reservoir, a neuronal cells channel having an abutment, a neuromuscular junction chamber that includes two pillars, and a gel seeding inlet.
Figure 14:
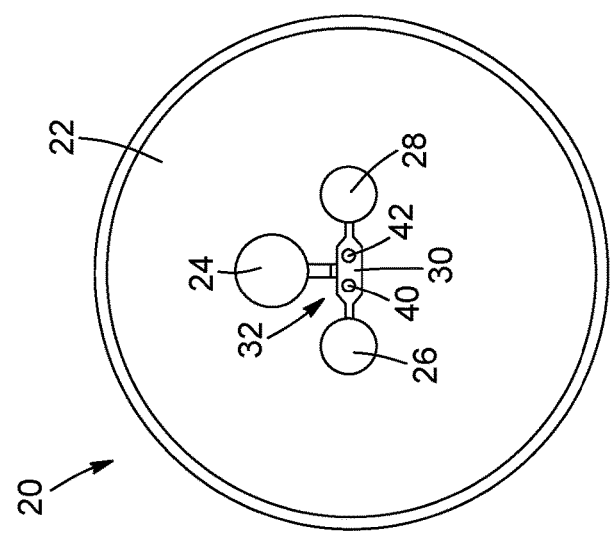
FIG. 14 is a bottom view of a cell culture device that includes a cell culture layer having a neuronal cells inlet, a first muscle cells reservoir, a second muscle cells reservoir, a neuronal cells channel having an abutment, and a neuromuscular junction chamber that includes two pillars.
Figure 16:
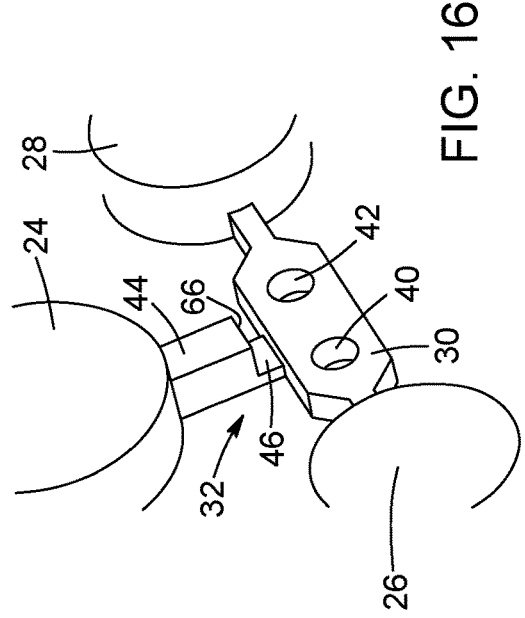
FIG. 16 is an enlarged front perspective view of a mold for producing the cell culture device shown in FIG. 14.
Figure 17:
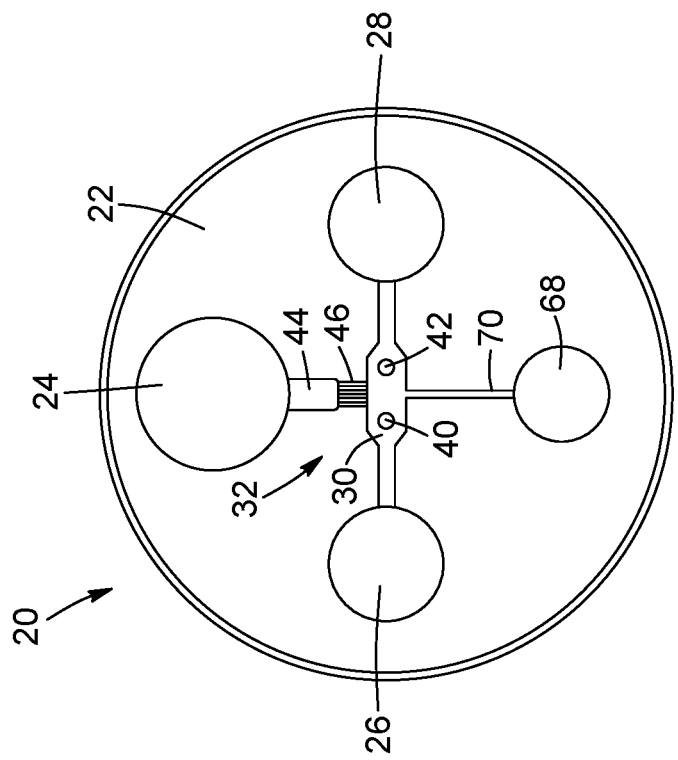
FIG. 17 is a bottom view of a cell culture device that includes a cell culture layer having a neuronal cells inlet, a first muscle cells reservoir, a second muscle cells reservoir, a neuronal cells channel having an abutment and including microchannels, a neuromuscular junction chamber that includes two pillars, and a gel seeding inlet.
Figure 23:
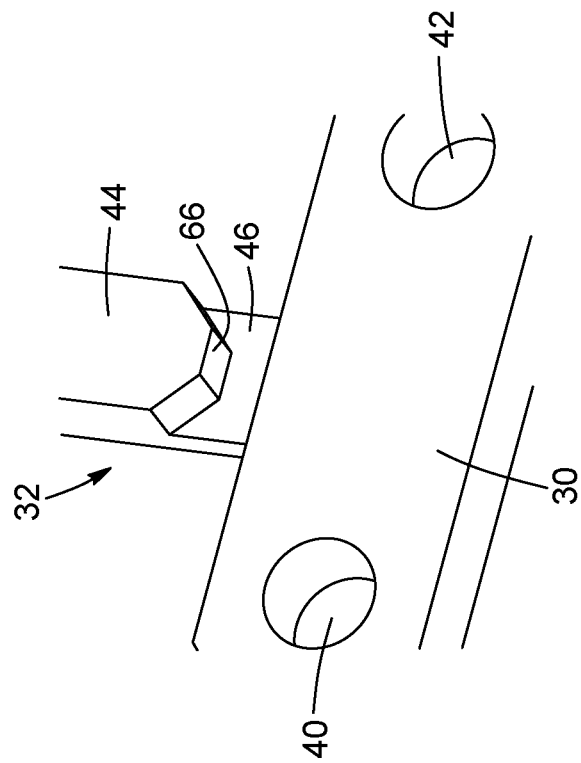
FIG. 23 is an enlarged front perspective view of a mold for producing the cell culture device shown in FIG. 22.
Figure 22:
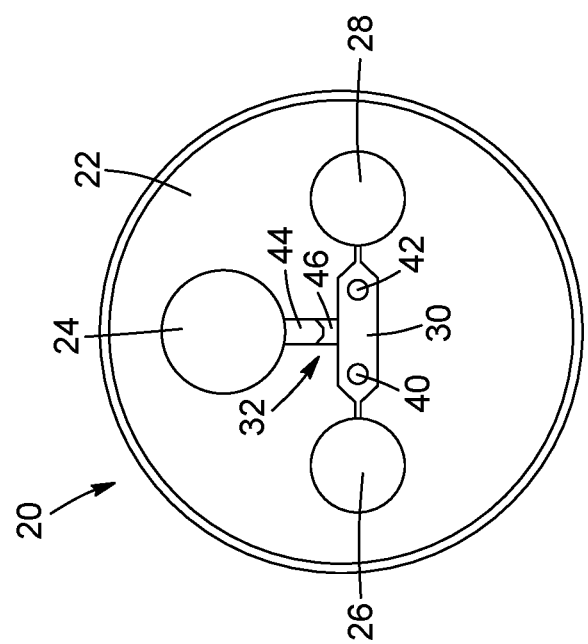
FIG. 22 is a bottom view of a cell culture device that includes a cell culture layer having a neuronal cells inlet, a first muscle cells reservoir, a second muscle cells reservoir, a neuronal cells channel having an abutment wall, and a neuromuscular junction chamber that includes two pillars.

Referring to FIGS. 15 and 17, in some implementations, the cell culture layer 22 can further include a gel seeding inlet 68 in fluid communication with the neuromuscular junction chamber 30 via a gel seeding channel 70. The gel seeding inlet 68 and associated gel seeding channel 70 can contribute to facilitate producing a neuromuscular junction that is embedded in a given matrix following addition of a gel solution to the gel seeding inlet 68. Thus, when a gel seeding inlet 68 is present, a gel solution that can include for instance Matrigel®, Geltrex®, fibrin, collagen, or other types of basement membrane matrix or extracellular membrane matrix (ECM), and suspended muscle cells can be seeded in the gel seeding inlet 68, and optionally, the gel solution can also be seeded in one of the first and second muscle cells reservoirs 26, 28, or in both the first and second muscle cells reservoirs 26, 28. In some implementations, the presence of the gel seeding inlet 68 can facilitate providing a higher degree of control with respect to the introduction and seeding of the muscle cells that will subsequently be present in the neuromuscular junction chamber 30.

Figure 18:
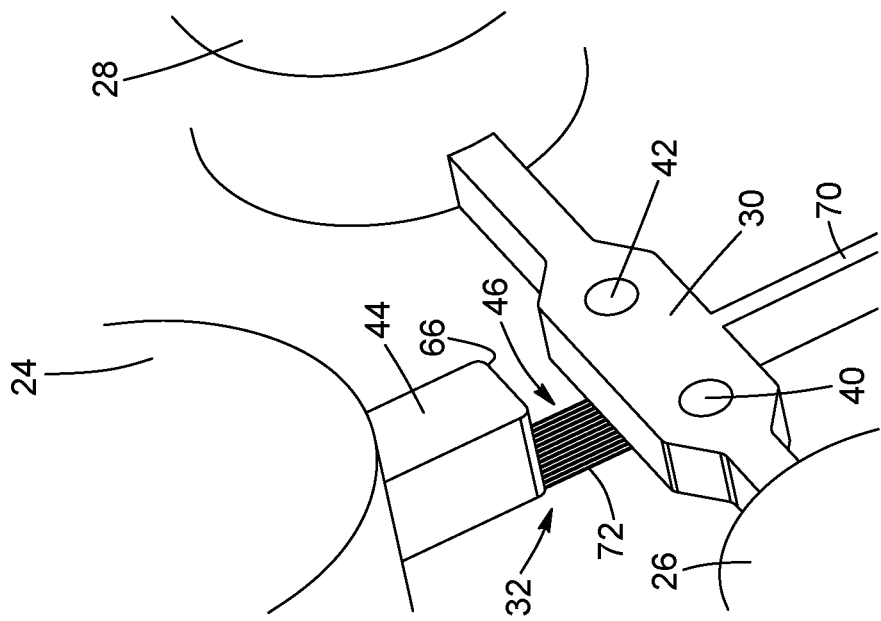
FIG. 18 is an enlarged front perspective view of the cell culture device of FIG. 17.

Referring to FIGS. 17 and 18, in some implementations, the second portion 46 of the neuronal cells channel 32 can include microchannels 72. The microchannels 72 of the second portion 46 have a reduced channel height h compared to the channel height h of the first portion 44. In the context of the present description, when referring to "microchannels", it is intended to mean that the channels can have for instance a width ranging from about 3 µm to about 500 µm, and a height ranging from about 3 µm to about 500 µm, to result in a cross section ranging from about 9 µm$^2$ to about 0.25 mm$^2$. It is important to note however that these ranges are given as examples only, and that other dimensions of the microchannels can also be implemented. In some implementations, the presence of the microchannels 72 can facilitate providing a preferential direction for axonal growth toward the neuromuscular junction chamber 30, and retaining the cell bodies of the one or more neurospheres within the first portion 44 of the neuronal cells channel 32. When the second portion 46 includes microchannels, techniques such as microfabrication or additive manufacturing, for instance, can be used to produce the cell culture layer 22. These techniques can also be used when the cell culture layer 22 is to be produced without microchannels.

Referring to FIGS. 19 to 21, the second portion 46, while having a reduced channel height h compared to the channel height h of the first portion 44, can include one or more channels located in peripheral regions of the second portion 46 of the neuronal cells channel 32. Referring more particularly to FIG. 21, the second portion 46 includes a first channel 74 located on a first side thereof, and a second channel 76 located on a second side thereof and opposed the first side, the first channel 74 and the second channel 76 being separated by a solid region extending across an entire channel height h of the second portion 46. In this implementation, the cell bodies of the one or more neurospheres can rest against the abutment wall 66, and the axons extending from the one or more neurospheres can extend within the first and second channels 74, 76 and reach the neuromuscular junction chamber 30 via second portion channel openings 78a, 78b, respectively.

It is to be understood that the illustrations shown in FIGS. 10, 13, 16, 18, 21 and 23 are schematic representations of a corresponding mold that would be used to produce a given cell culture layer, and are thus to be interpreted accordingly, with the void spaces having to be considered as filled and the solid features having to be considered as void spaces, to obtain a representation of the given cell culture layer.

Figure 28B:
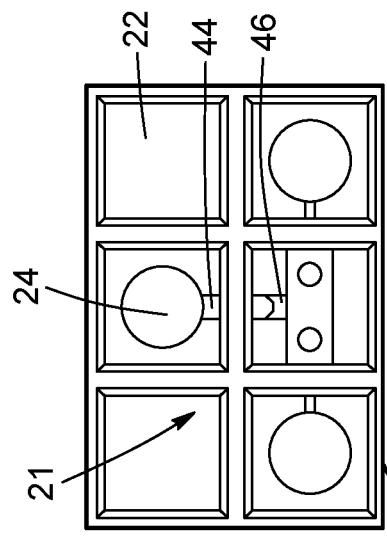
FIG. 28B is an enlarged top view of another portion of the cell culture layer and cell culture plate of FIG. 28, the portion including a NMJ preparation unit that includes a single neuronal cells inlet.
Figure 28A:
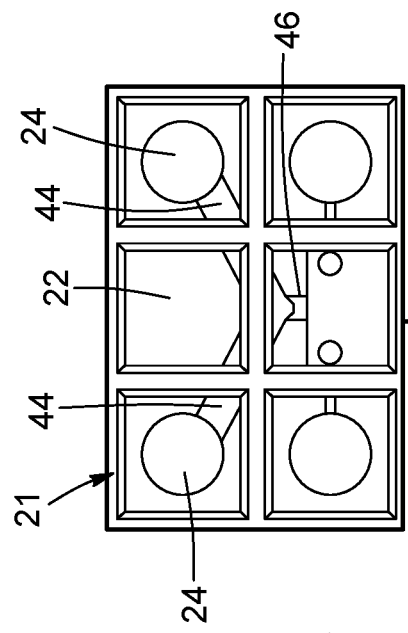
FIG. 28A is an enlarged top view of a portion of the cell culture layer and cell culture plate of FIG. 28, the portion including a NMJ preparation unit that includes two neuronal cells inlets.
Figure 28:
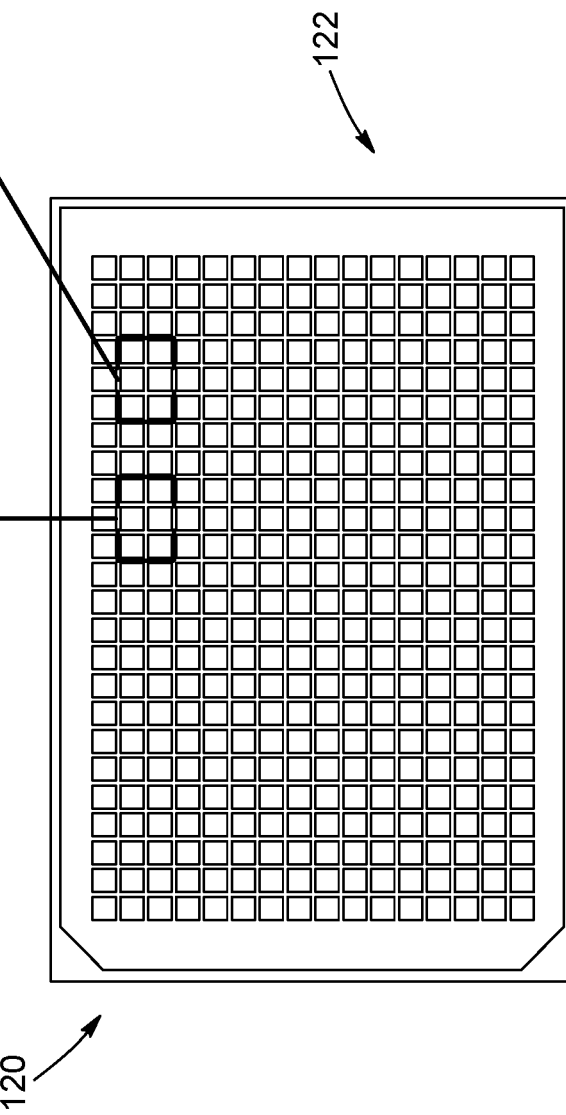
FIG. 28 is a top view of a cell culture layer in combination with a cell culture plate that includes a multi-grid layer and a base layer.

FIG. 28 illustrates an example of a cell culture layer 22 used with a cell culture plate 120 that includes a multi-well grid layer 122 and a base layer (not shown). In the implementation shown, the cell culture layer 22 includes two types of NMJ preparation units. The NMJ preparation unit identified as "B" is similar to the NMJ preparation unit shown in FIG. 1. The NMJ preparation unit identified as "A" differs from the one identified as "B" in that it includes two neuronal cells inlets 24. Given the presence of the two neuronal cells inlets 24, the neuronal cells channel 32 includes two first portions 44 that combine as a single second portion 46, downstream of the two first portions 44. Thus, each one of the first portions 44 of the neuronal cells channel 32 is connected to a corresponding one of the neuronal cells inlet 34.

Figure 29A:
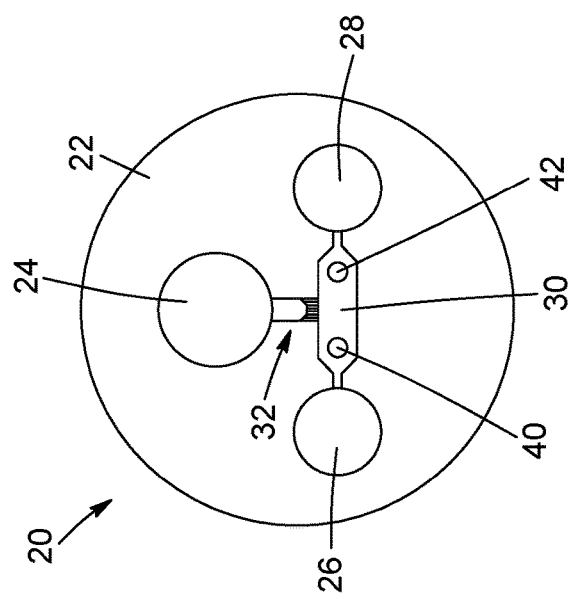
FIG. 29A is a bottom view of a cell culture device that includes a cell culture layer having a neuronal cells inlet, a first muscle cells reservoir, a second muscle cells reservoir, a neuronal cells channel having an abutment wall, a neuromuscular junction chamber that includes two pillars and longitudinally extending supports provided in a second portion of the neuronal cells channel.
Figure 29C:
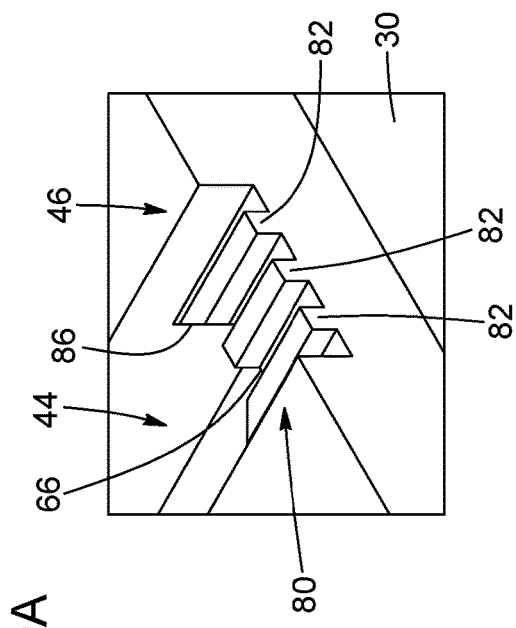
FIG. 29C is an enlarged view of the neuronal cells channel of the cell culture layer of FIG. 29A.
Figure 29B:
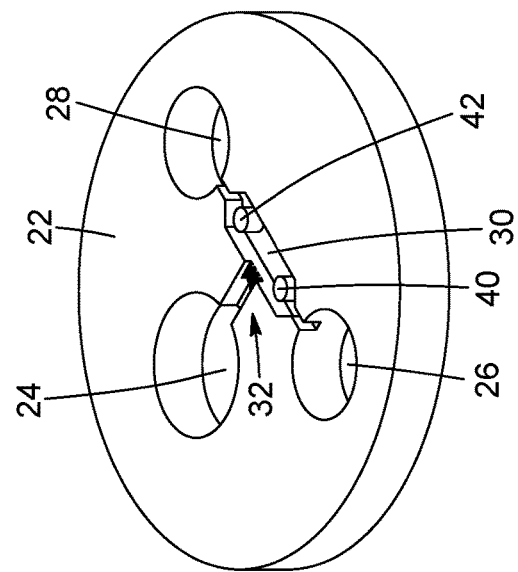
FIG. 29B is a bottom perspective view of the cell culture device of FIG. 29A.

FIG. 29 illustrates an example of a cell culture device 20 that includes a cell culture layer 22, the cell culture layer 22 including a neuronal cells inlet 24, a first muscle cells reservoir 26, a second muscle cells reservoir 28, and a neuronal cells channel 32 extending between the neuronal cells inlet 24 and the neuromuscular junction chamber 30. The neuronal cells channel 32 includes a first portion 44 having a first portion cross-section, and a second portion 46, provided downstream of the first portion 44 and having a second portion cross-section. In this implementation, the second portion 46 of the neuronal cells channel 32 includes longitudinally extending supports 80 configured as rectangularly-shaped supports 82. The longitudinally extending supports 80 are spaced apart from each other to define channels therebetween. The longitudinally extending supports 80 extend longitudinally along the length of the neuronal cells channel 32, and further contribute to reduce the second portion cross-section of the second portion 46 of the neuronal cells channel 32 while enabling the neuronal extensions of the neurosphere to reach the neuromuscular junction chamber 30. In some implementations, the presence of the longitudinally extending supports 80 can contribute to further stabilize the portion of the neurosphere that contains the neuronal cell bodies in the first portion 44 of the neuronal cells channels 32, i.e., to prevent its downstream movement toward the neuromuscular junction chamber 30. In this implementation, the rectangularly-shaped supports 82 have respective upstream transversal surfaces 86 that are substantially aligned with the abutment wall 66 of the neuronal cells channels 32. It is to be understood that in other implementations, the respective upstream transversal surfaces 86 can also be aligned differently with respect to the abutment wall 66 of the neuronal cells channels 32.

Figure 30A:
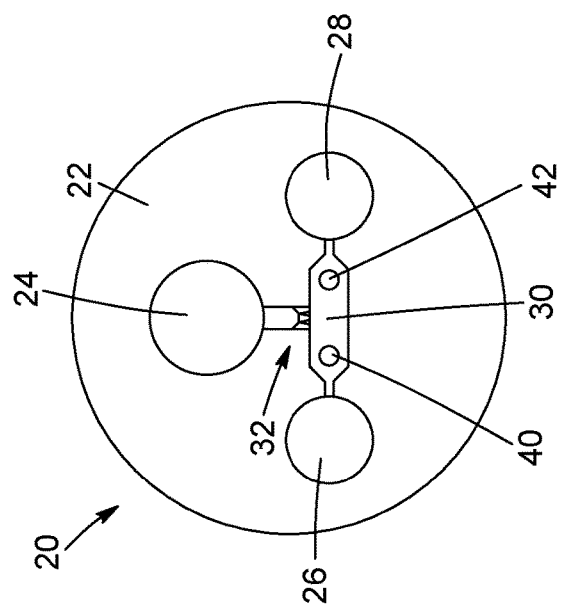
FIG. 30A is a bottom view of a cell culture device that includes a cell culture layer having a neuronal cells inlet, a first muscle cells reservoir, a second muscle cells reservoir, a neuronal cells channel having an abutment wall, a neuromuscular junction chamber that includes two pillars and longitudinally extending supports provided in a second portion of the neuronal cells channel.
Figure 30C:
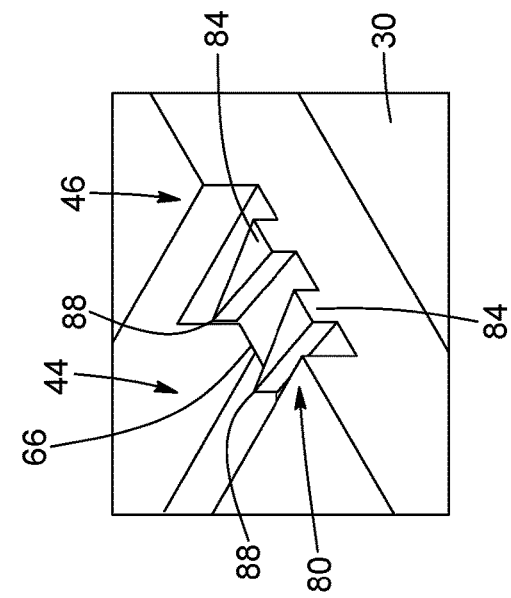
FIG. 30C is an enlarged view of the neuronal cells channel of the cell culture layer of FIG. 30A.
Figure 30B:
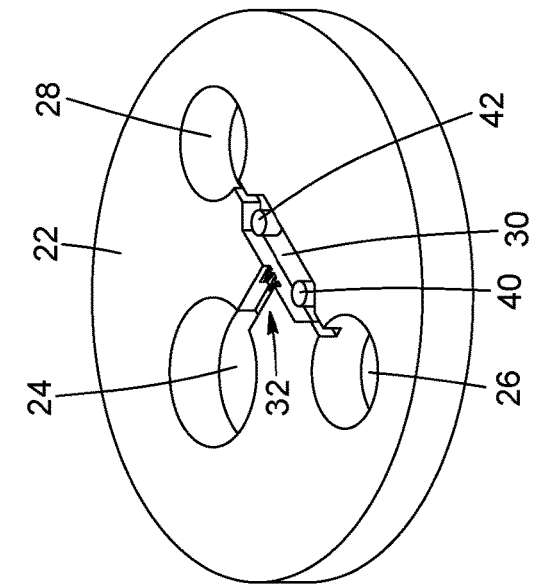
FIG. 30B is a bottom perspective view of the cell culture device of FIG. 30A.

FIG. 30 illustrates a similar implementation as in FIG. 29, although the longitudinally extending supports 80 are provided as triangularly-shaped supports 84. In this implementation, the peaks 88 (or top edge) of the triangularly-shaped supports 84 are provided so as to coincide with a respective transition between two adjacent surfaces of the abutment wall 66 of the neuronal cells channels 32. It is to be understood that in other implementations, the respective peaks 88 can also be aligned differently with respect to the abutment wall 66 of the neuronal cells channels 32.

Figure 31A:
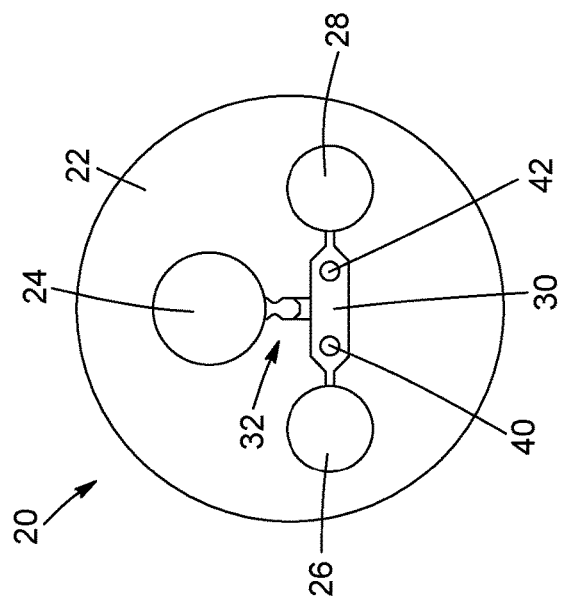
FIG. 31A is a bottom view of a cell culture device that includes a cell culture layer having a neuronal cells inlet, a first muscle cells reservoir, a second muscle cells reservoir, a neuronal cells channel having an abutment wall and an hourglass section, a neuromuscular junction chamber that includes two pillars.
Figure 31C:
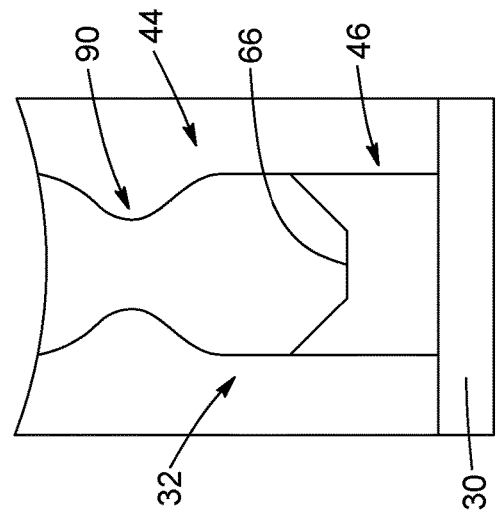
FIG. 31C is an enlarged view of the neuronal cells channel of the cell culture layer of FIG. 31A.
Figure 31B:
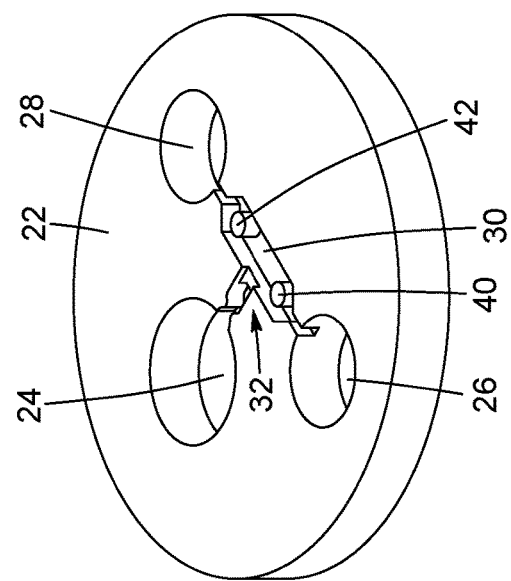
FIG. 31B is a bottom perspective view of the cell culture device of FIG. 31A.

FIG. 31 illustrates an example of a cell culture device 20 that includes a cell culture layer 22, the cell culture layer 22 including a neuronal cells inlet 24, a first muscle cells reservoir 26, a second muscle cells reservoir 28, and a neuronal cells channel 32 extending between the neuronal cells inlet 24 and the neuromuscular junction chamber 30. The neuronal cells channel 32 includes a first portion 44 having a first portion cross-section, and a second portion 46, provided downstream of the first portion 44 and having a second portion cross-section. In this implementation, the first portion 44 of the neuronal cells channel 32 includes an hourglass section 90. The hourglass section 90 contributes to reduce the width w of the first portion 44 of the neuronal cells channels 32. In some implementations, the presence of the hourglass section 90 can contribute to further stabilize the portion of the neurosphere that contains the neuronal cell bodies in the first portion 44 of the neuronal cells channels 32 by preventing its upstream movement toward the neuronal cells inlet 24.

Figure 33A:
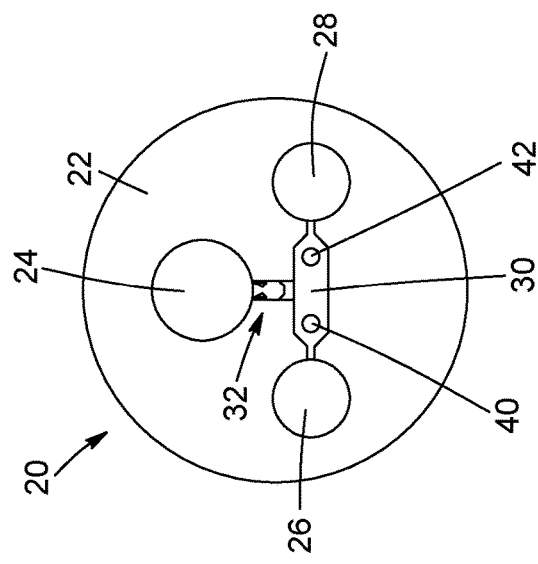
FIG. 33A is a bottom view of a cell culture device that includes a cell culture layer having a neuronal cells inlet, a first muscle cells reservoir, a second muscle cells reservoir, a neuronal cells channel having an abutment wall, a neuromuscular junction chamber that includes two pillars and posts provided in a first portion of the neuronal cells channel.
Figure 33C:
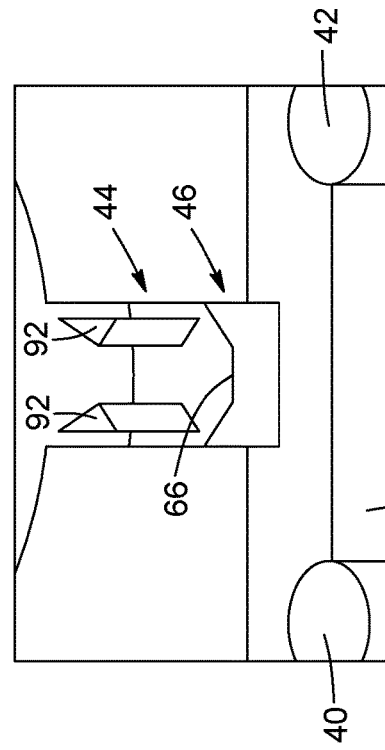
FIG. 33C is an enlarged view of the neuronal cells channel of the cell culture layer of FIG. 33A.
Figure 33B:
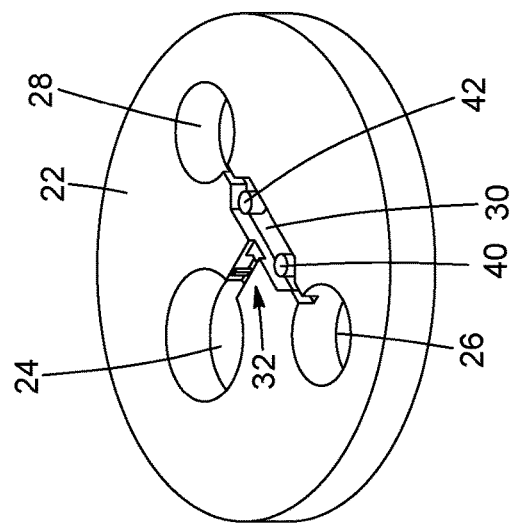
FIG. 33B is a bottom perspective view of the cell culture device of FIG. 33A.

FIGS. 32 and 33 illustrate examples of a cell culture device 20 that includes a cell culture layer 22, the cell culture layer 22 including a neuronal cells inlet 24, a first muscle cells reservoir 26, a second muscle cells reservoir 28, and a neuronal cells channel 32 extending between the neuronal cells inlet 24 and the neuromuscular junction chamber 30. The neuronal cells channel 32 includes a first portion 44 having a first portion cross-section, and a second portion 46, provided downstream of the first portion 44 and having a second portion cross-section. In this implementation, the first portion 44 of the neuronal cells channel 32 includes posts 92 configured as triangularly-shaped posts, the posts 92 being spaced apart from each other. The posts 92 extend downwardly from a top surface of the first portion 44 of the neuronal cells channel 32 (with reference to when the cell culture layer is deposited onto a substantially horizontal surface), and are provided at a given location along the length of the neuronal cells channel 32 so that the neurosphere can ended up being located between the posts 92 and the abutment wall 66. The posts 92 can thus further contribute to stabilize the neurosphere in the neuronal cells channel 32, and more particularly to maintain the portion of the neurosphere that contains the neuronal cell bodies in the first portion 44 of the neuronal cells channels 32 by preventing its upstream movement toward the neuronal cells inlet 24. The shape of the posts 92 can vary. In the implementation shown in FIG. 32, the posts 92 are shaped as regular triangular prisms (base includes an equilateral triangle), whereas in the implementation shown in FIG. 33, the posts 92 are shaped as irregular triangular prisms (base includes a triangle that is not equilateral). It is to be understood that in other implementations, the posts 92 can also be shaped differently than shown in FIGS. 32 and 33. For instance, the posts 92 can be shaped as rectangular prisms or as cylinders.

Several alternative implementations and examples have been described and illustrated herein. The implementations of the technology described above are intended to be exemplary only. A person of ordinary skill in the art would appreciate the features of the individual implementations, and the possible combinations and variations of the components. A person of ordinary skill in the art would further appreciate that any of the implementations could be provided in any combination with the other implementations disclosed herein. It is understood that the technology may be embodied in other specific forms without departing from the central characteristics thereof. The present implementations and examples, therefore, are to be considered in all respects as illustrative and not restrictive, and the technology is not to be limited to the details given herein. Accordingly, while the specific implementations have been illustrated and described, numerous modifications come to mind.

The invention claimed is:

1. A cell culture device for preparing an in vitro model of a neuromuscular junction, the cell culture device comprising:
   a cell culture layer comprising:
      a single neuronal cells inlet configured for receiving neuronal cells therein;
      first and second muscle cells reservoirs, wherein at least one of the first and second muscle cells reservoirs is configured for seeding muscle cells and receive a muscle cells reservoir fluid therein, the single neuronal cells inlet and the first and second muscle cells reservoirs together forming vertices of a triangular shape;
      a neuromuscular junction chamber extending between the first and second muscle cells reservoirs and in fluid communication therewith to enable co-culture of the neuronal cells with the muscle cells to form the neuromuscular junction;
      an anchoring point provided in the neuromuscular junction chamber to provide an anchor for the muscle cells and enable formation of muscle fibers and anchoring thereof; and
      a single neuronal cells channel associated with the single neuronal cells inlet and extending between the single neuronal cells inlet and the neuromuscular junction chamber and in fluid communication therewith, the neuronal cells channel comprising:
         a first portion having a first portion cross-section sized to retain neural cell bodies of the neuronal cells, the first portion comprising first portion sidewalls, a first portion front wall and a first portion back wall; and
         a second portion provided downstream of the first portion and directly opening into the neuromuscular junction chamber, the second portion having a second portion cross-section smaller than the first portion cross-section and that is sized to prevent entry of the neural cell bodies therein, the second portion comprising second portion sidewalls, a second portion front wall and a second portion back wall.

2. The cell culture device of claim 1, wherein a sidewall transition from the first portion sidewalls to the second portion sidewalls is substantially linear, such that the neuronal cells channel has a channel width that is substantially the same when transitioning from the first portion to the second portion.

3. The cell culture device of claim 1, further comprising a cell culture dish, a cell culture plate or a microscope slide having a cell culture layer receiving surface onto which the cell culture layer is deposited, and wherein the first portion back wall and/or the second portion back wall is provided by the cell culture layer receiving surface of the cell culture dish, the cell culture plate or the microscope slide.

4. The cell culture device of claim 3, wherein the second portion front wall is provided inwardly from the first portion front wall, such that the neuronal cells channel has a channel height that is smaller in the second portion compared to the first portion, thereby providing at least in part the smaller second portion cross-section compared to the first portion cross-section.

5. The cell culture device of claim 1, wherein the second portion front wall is provided inwardly from the first portion front wall and/or the second portion back wall is provided inwardly from the first portion back wall, such that the neuronal cells channel has a channel height that is smaller in the second portion compared to the first portion, thereby providing the smaller second portion cross-section compared to the first portion cross-section.

6. The cell culture device of claim 1, wherein a transition from the first portion front wall to the second portion front wall comprises a step change from the first portion front wall defining an abutting wall extending transversally across the neuronal cells channel.

7. The cell culture device of claim 6, wherein the abutting wall converges inwardly toward a centerline of the neuronal cells channel.

8. The cell culture device of claim 1, wherein the anchoring point comprises a first pillar provided in the neuromuscular junction chamber in proximity of the first muscle cells reservoir and a second pillar provided in the neuromuscular junction chamber in proximity of the second muscle cells reservoir, the first and second pillars extending upwardly.

9. The cell culture device of claim 1, further comprising a gel seeding inlet in fluid communication with the neuromuscular junction chamber and opposed to the neuronal cells inlet, the gel seeding inlet being configured to seed gel in the neuromuscular junction chamber.

10. The cell culture device of claim 1, wherein the neuronal cells are provided as a cluster of neuronal cell bodies and include axons extending away from the cell bodies, the first portion of the neuronal cells channel being configured to receive the cluster of cell bodies and the second portion of the neuronal cells channel being configured to direct the axons toward the neuromuscular junction chamber.

11. The cell culture device of claim 1, wherein the second portion of the neuronal cells channel comprises microchannels for directing axonal growth.

12. The cell culture device of claim 1, further comprising an electrode provided in proximity of the cell culture layer.

13. The cell culture device of claim 12, wherein the electrode forms part of an electrode layer located underneath the cell culture layer, superposed to the cell culture layer or integrated in the cell culture layer.

14. A cell culture device for preparing an in vitro model of a neuromuscular junction, the cell culture device comprising:
   a cell culture layer comprising:
      a single neuronal cells inlet configured for receiving neuronal cells therein;
      first and second muscle cells reservoirs, wherein at least one of the first and second muscle cells reservoirs is configured for seeding muscle cells and receive a muscle cells reservoir fluid therein;
      a neuromuscular junction chamber extending between the first and second muscle cells reservoirs and in fluid communication therewith to enable co-culture of the neuronal cells with the muscle cells to form the neuromuscular junction; and
      a single neuronal cells channel associated with the single neuronal cells inlet and extending between the single neuronal cells inlet and the neuromuscular junction chamber and in fluid communication therewith, the neuronal cells channel comprising:
  a first portion having a first portion cross-section sized to retain neural cell bodies of the neuronal cells, the first portion comprising first portion sidewalls, a first portion front wall, a first portion back wall and a first second channel height; and
  a second portion provided downstream of the first portion, the second portion having a second portion cross-section smaller than the first portion cross-section and that is sized to prevent entry of the neural cell bodies therein, the second portion comprising second portion sidewalls, a second portion front wall, a second portion back wall and a second portion channel height;
  wherein a transition from the first portion front wall to the second portion front wall comprises a step change defining an abutting wall extending transversally across the neuronal cells channel such that the second portion channel height is smaller than the first second channel height.

15. The cell culture device of claim 14, wherein the abutting wall converges inwardly toward a centerline of the neuronal cells channel.

16. The cell culture device of claim 14, wherein the first portion sidewalls, the first portion front wall and the first portion back wall define a first opening of the neuronal cells channel into the neuronal cells inlet, and the second portion sidewalls, the second portion front wall and the second portion back wall define a second opening of the neuronal cells channel into the neuromuscular junction chamber.

17. The cell culture device of claim 14, wherein a sidewall transition from the first portion sidewalls to the second portion sidewalls is substantially linear, such that the neuronal cells channel has a channel width that is substantially the same between the first portion and the second portion.

18. The cell culture device of claim 14, further comprising a cell culture dish, a cell culture plate or a microscope slide having a cell culture layer receiving surface onto which the cell culture layer is deposited, and wherein the first portion back wall and/or the second portion back wall is provided by the cell culture layer receiving surface of the cell culture dish, the cell culture plate or the microscope slide.

19. The cell culture device of claim 14, wherein the second portion of the neuronal cells channel comprises a plurality of channels.

20. The cell culture device of claim 14, wherein the second portion of the neuronal cells channel comprises microchannels for directing axonal growth.

21. The cell culture device of claim 14, wherein the second portion of the neuronal cells channel comprises spaced-apart posts extending downwardly from the first portion front wall, the spaced-apart posts being located at a given distance from the abutment wall such to enable the neuronal bodies to be received between the abutment wall and the spaced-apart posts.

22. The cell culture device of claim 14, further comprising:
  a first pillar provided in the neuromuscular junction chamber in proximity of the first muscle cells reservoir; and
  a second pillar provided in the neuromuscular junction chamber in proximity of the second muscle cells reservoir, the first and second pillars extending upwardly and serving as respective anchoring locations for the muscle cells;
  wherein the second portion of the neuronal cells channel opens up into the neuromuscular junction chamber at a location that is located between the first and second pillars.

23. The cell culture device of claim 14, further comprising a gel seeding inlet in fluid communication with the neuromuscular junction chamber and opposed to the neuronal cells inlet, the gel seeding inlet being configured to seed gel in the neuromuscular junction chamber.

24. The cell culture device of claim 14, wherein the neuronal cells are provided as a cluster of neuronal cell bodies and include axons extending away from the cell bodies, the first portion of the neuronal cells channel being configured to receive the cluster of cell bodies and the second portion of the neuronal cells channel being configured to direct the axons toward the neuromuscular junction chamber.

25. The cell culture device of claim 14, further comprising an electrode provided in proximity of the cell culture layer.

26. The cell culture device of claim 25, wherein the electrode forms part of an electrode layer located underneath the cell culture layer, superposed to the cell culture layer or integrated in the cell culture layer.

* * * * *